United States Patent
Rogers et al.

(10) Patent No.: US 6,346,706 B1
(45) Date of Patent: Feb. 12, 2002

(54) HIGH RESOLUTION PHOTON DETECTOR

(75) Inventors: William L. Rogers; Neal H. Clinthorne, both of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/344,156

(22) Filed: Jun. 24, 1999

(51) Int. Cl.[7] ............................................... G01T 1/166
(52) U.S. Cl. ............................. 250/363.04; 250/363.01; 378/4
(58) Field of Search ................. 250/363.04, 363.01, 250/361 R, 363.03, 377.09; 378/4, 21

(56) References Cited

U.S. PATENT DOCUMENTS

| | | |
|---|---|---|
| 4,015,592 A | 4/1977 | Bradley-Moore |
| 4,980,552 A | * 12/1990 | Cho et al. ............... 250/363.03 |
| 5,210,421 A | * 5/1993 | Gullberg ................ 250/363.04 |
| 6,140,649 A | * 10/2000 | Lonn ..................... 250/363.04 |

FOREIGN PATENT DOCUMENTS

| | | |
|---|---|---|
| DE | 0 603 110 | 6/1994 |
| WO | 95/03554 | 2/1995 |

* cited by examiner

*Primary Examiner*—Robert H. Kim
*Assistant Examiner*—Pamela R. Hobden
(74) *Attorney, Agent, or Firm*—Quarles & Brady, LLP

(57) ABSTRACT

An apparatus for identifying the location of a photon source within an imaging area and which generates photons having energies within a known energy range, the apparatus including two oppositely facing cameras disposed on opposite sides of the imaging area, each camera including a first detector unit which causes scattering when a photon enters the unit and generates signals indicative of the scattering event location, energy and time and a second detector unit which absorbs the scattered photon and generates signals indicative of the absorption event energy and time, the generated signals are then mathematically combined to determine the location of the source. Also a Compton camera including a first detector unit which is anatomically configured to generally mirror the external surface of a portion of a patient including an object to be imaged, a second detector unit positioned outside an imaging area to receive scattered photons from the first unit.

45 Claims, 7 Drawing Sheets

HIGH RESOLUTION PHOTON DETECTOR

STATEMENT REGARDING FEDERALLY SPONSORED RESEARCH OR DEVELOPMENT

This invention was supported by a DHHS under NIH grant R01 CA32846, "Radionuclides: Quantification and Measurement, Principal investigator: W. L. Rogers."

CROSS-REFERENCE TO RELATED APPLICATIONS

Not applicable.

BACKGROUND OF THE INVENTION

The present invention relates to imaging systems and more particularly to an imaging system including at least two detectors, a first detector being a high resolution detector which detects energy and location of Compton scatters and a second detector being a residual energy detector.

Radionuclides are decaying substances which emit subatomic particles (e.g. beta particles, alpha particles, neutrons, positrons and/or photons). For example single photon emitters such as Technetium emit photons and perhaps also a charged particle wherein there is no angular correlation between multiple emitted photons. As another example, Fluorine-18 decays to Oxygen-17 by emitting a positron which has an energy between 0 and 600 keV with a mean energy of 250 keV.

Radionuclides are employed as radioactive tracers called "radiopharmaceuticals" by incorporating them into substances such as glucose or carbon dioxide. One common use for radiopharmaceuticals is in the medical imaging field. To use a radiopharmaceutical in imaging, the radiopharmaceutical is injected into a patient and accumulates in an organ, vessel or the like, which is to be imaged. Hereinafter an exemplary radionuclide in an exemplary radiopharmaceutical used for imaging will be referred to as an imaging radionuclide.

It is known that specific radiopharmaceuticals become concentrated within certain organs. The process of concentrating often involves processes such as glucose metabolism, fatty acid metabolism and protein synthesis. Hereinafter, an organ to be imaged will be referred to generally as an "organ of interest" and prior art and the invention will be described with respect to a hypothetical organ of interest.

After a radiopharmaceutical becomes concentrated within an organ of interest and while the imaging radionuclides decay, the radionuclides emit subatomic particles including positrons and photons. Each of the particles and photons can be detected. Where the particles are positrons, the positrons travel very short distances (e.g., approximately 200 microns in the case of Flourine-18) before they encounter an electron and, when a positron encounters an electron, the positron is annihilated as the electron and positron unite and two photons are generated.

Photons are characterized by one feature which is pertinent to all medical imaging techniques which sense photons. Given a specific radionuclide, photons generated directly from decay or via decay followed by annihilation, have specific and known energy levels. For example, when a positron results from decay of Fluorine-18, annihilation of the positron always results in two photons, each of which has an energy of 511 keV. As other examples, $^{131}I$ generates photons having energies of 360 keV while $^{99m}T_c$ generates photons having energies of 140 keV. In addition, particle annihilation events are characterized by an additional feature which is pertinent to medical imaging. This additional feature is that, upon an annihilation event, two photons are generated and the photons are directed in essentially opposite directions (i.e. the trajectories are separated by approximately 180°). There is approximately a ±0.25 degree variation from 180° in the photon trajectories related to the momentum of the electron-positron pair before annihilation.

In all photon imaging systems both photon energy and trajectory have to be determined. Photon energy is determined and compared to a range of expected energies associated with the particular radiopharmaceutical used during data generation. Where sensed energy is outside the expected range the detection is typically discarded. Where sensed energy is within the expected range, the detection is identified as valid, photon trajectory is determined and trajectories for all valid detections are combined to generate an image of the object of interest.

Three different imaging systems which are pertinent to the present invention include PET, collimated single photon imaging and Compton imaging systems, each of which is described separately below.

PET Systems

An exemplary PET system includes two oppositely facing cameras wherein the cameras are either scintillation cameras or solid state direct conversion detector (DCD) cameras.

An exemplary scintillation camera includes a plurality of detector units and a processor which, among other things, includes coincidence detection circuitry. An exemplary detector unit includes a two dimensional 6×6 matrix of bismuth germinate (BGO) scintillator crystals which are disposed in front of four photo multiplier tubes (PMTs). When a crystal absorbs a photon, the crystal generates light which is generally directed toward the PMTs. The PMTs absorb the light and each PMT produces an analog signal which arises sharply when a scintillation event occurs and then tails off exponentially with a time constant of approximately 300 nanoseconds. The relative magnitudes of the analog PMT signals are determined by the position in the 6×6 BGO matrix of the crystal which generates the light (i.e., where the scintillation event takes place), and the total magnitude of these signals is determined by the energy of the photon which causes an event.

For each total magnitude within a range of expected magnitudes corresponding to the imaging radionuclide, a set of acquisition circuits receives the PMT signals and determines x and y event coordinates within the BGO matrix thereby determining the crystal which absorbed the photon and the general x-y coordinate at which the absorption occurred on the face of the crystal. Each acquisition circuit also produces an event detection pulse (EDP) which indicates the exact moment at which a scintillation event took place.

The information regarding each valid event is assembled into a digital event data packet which indicates precisely when the event took place and the position of the BGO crystal which detected the event. Event data packets are conveyed to a coincidence detector which determines if any two events from the opposing detectors are in coincidence.

Coincidence is determined by a number of factors. First, the time markers in each event data packet must be within a specific time window of each other, and second, the locations indicated by the two event data packets must lie on a straight line which passes through the field of view of a scanner imaging area. Events which cannot be paired as coincidence events are discarded, but coincidence event pairs are located and recorded as coincidence data packets. Each coincidence data packet includes a pair of digital numbers which precisely identify the addresses of the two BGO crystals that detected the event. After an event pair has been identified, the source location of the pair can be identified along a straight line which passes through the locations of the events in the pair. After imaging data has been collected in this manner, a processor uses the collected information to generate a two or three dimensional image of the organ of interest.

DCDs may be based on pixilated semiconductor detectors such as Cadmium Telluride (CdTe) or Cadmium Zinc Telluride (CdZnTe) devices. Generally, each DCD includes an absorption member, a cathode, at least one anode, a potential biasing mechanism (i.e. voltage source) and a separate amplifier for each anode.

The absorption member is formed of a planar semiconductor material (e.g. CdTe or CdZnTe) which has oppositely facing cathode and anode surfaces. The dimension between the cathode and anode surfaces is an absorption member thickness. When photons are directed at the cathode surface, the photons penetrate the absorption member and each photon is absorbed at an absorption depth within the member thickness. When a photon interacts with the absorption member while being absorbed, the absorption member generates a plurality of electrons and holes.

The cathode is attached to and essentially covers the cathode surface and the anode is attached to the anode surface. The biasing mechanism is linked to the cathode and biases the cathode negative. The anode remains unbiased and therefore is positive with respect to the cathode. Because the cathode is negative and the anode is positive with respect to the cathode, when electrons and holes are generated during absorption, the holes are attracted to the cathode surface and the electrons are attracted to the anode surface. The electrons generate a first negative charge component on the anode.

As holes accumulate at the cathode, the positive charge adjacent the cathode causes a capacitive second negative charge component on the anode. To distinguish between the first negative charge component on the anode caused by electrons which travel from the absorption depth to the anode and the second negative charge component on the anode caused by the holes, the first negative charge component will be referred to hereinafter as the electron charge and the second negative charge component will be referred to hereinafter as the hole charge. Together, the electron charge and the hole charge are referred to hereinafter as the collected charge.

The amplifier is attached to the anode and includes an output lead for providing an anode signal indicating the collected charge. The amplifier output lead is linked to a camera processor. The processor integrates the anode signal over an integration period and provides an intensity signal. The processor compares the intensity signal to an expected intensity signal or expected energy range (e.g., 511 keV) associated with the imaging radionuclide. When an intensity signal is within the expected range, the processor indicates that a photon has been detected by the DCD which provided the anode signal.

As with the scintillation camera, DCD cameras provide photon detection signals to coincidence circuitry which in turn identifies coincident pairs of photons and stores the coincident pairs as coincident data packets for subsequent image processing.

Two important criteria for any imaging system are resolution and sensitivity. Resolution is a term used to refer to position accuracy of a sensed interaction or energy deposit. In other words, resolution measures how close a perceived absorption point is to an actual absorption point. Sensitivity is a term used to refer to the percentage of photons within an expected energy range emanating toward a camera which are actually detected to be valid events. High sensitivity is better than low sensitivity. For example, a sensitivity of 20% (i.e., 1 in 5 photons are detected) is better than a sensitivity of 10%.

The resolution criteria favors selecting a radiopharmaceutical which generates relatively low energy photons. Three sources of resolution degradation include Compton scattering, depth-of interaction variances and incident angle errors. As well known in the imaging arts, in addition to complete absorption, a second type of interaction referred to as "Compton scattering" often takes place within an absorption member or scintillation crystal. Hereinafter, the term "absorption member" will be used generically to refer to either a solid state absorption member or a scintillation crystal. When a photon enters an absorption member, the photon may experience a first interaction in which photon direction is altered and only a portion of photon energy is absorbed. Thereafter, the photon may exit the absorption member without being fully absorbed, Compton scatter one or more additional times prior to full absorption, or may be fully absorbed at some other location within the member upon a second interaction.

To increase the likelihood of full absorption and hence the sensitivity of a detector, most PET detectors are designed to have relatively thick absorption members. In this manner, while a photon may "rattle" around in the member from one Compton scattering to the next prior to complete absorption, the entire photon energy will be sensed and therefore the energy will be within the expected energy window.

Where photon energy is absorbed at several different locations (i.e. one or more Compton scatters occur prior to final absorption), the location of the first interaction or absorption is difficult and, in some cases, impossible to determine. For instance, referring to FIG. 1, an exemplary absorption member 10 is illustrated which includes an entry face 11. A photon 12 emanates from an object of interest (not illustrated) and travels along a path 14 into member 10 through an entry point X in face 11 and a single Compton scatter occurs at point A. The scattered photon traverses along a path essentially parallel to face 11 prior to a complete absorption of residual photon energy at point B. In the case of these two interactions the entry point is perceived to be located at the "center of gravity" of the two energy depositions. For example, if deposition B is much greater than deposition A, the perceived entry point is close to Y. The potential for error increases as the number of Compton scatters increases.

With respect to depth-of-interaction errors, referring still to FIG. 1, an absorption may occur at any depth within the thickness of absorption member 10. The coordinate detection circuitry is set up to identify an x-y coordinate pair (i.e. a point on face 11) corresponding to the center of gravity of all related depositions. This type of detection works well for photons which enter absorption member 10 perpendicular to face 11 but results in position errors where photons enter the member at an angle with respect to face 11. For example, assume a photon 16 enters member 10 at a 45 degree angle with respect to face 11 at point C and traverses along a path 17 to point D prior to full absorption. In this case instead of identifying point C as the location at which photon 16 entered face 11, detector circuitry identifies a face entry point E associated with point D. Once again an error occurs.

With respect to incident angle errors, in PET systems, as indicated above, while photons generated by a single annihilation travel essentially in opposite directions (i.e. along trajectories which are 180° apart), there is some variation (i.e. ±0.25 degrees) from the 180° assumption. Because of this variation, the location of an annihilation identified via a PET system often has some slight error. For example, where PET cameras are one meter apart, 0.25 degrees variation translated into ±2 mm halfway between the detectors.

As well known in the imaging industry, when a radionuclide which generates low energy photons is used for imaging, the probability of interaction within an absorption member is relatively high, absorption typically occurs upon a first interaction and the first interaction typically occurs at a relatively shallow depth within the absorption member. For these reasons Compton scatter and depth-of-interaction variances do not appreciably effect quality when low energy photons are employed.

As incident photon energy increases, the probability of a complete absorption drops very fast while the probability of Compton scattering drops more slowly. Consequently, at 511 keV, for example, a large fraction of photons which are completely absorbed within a member will Compton scatter during a first interaction and are subsequently absorbed somewhere else within the member. In addition, at 511 keV, photons are likely to travel tens of millimeters in most detectors prior to interaction and therefore depth-of-interaction variances tend to distort final images.

In any event, Compton scattering, depth of interaction variances and incident angle variances combined when imaging with medium to high energy photons result in relatively poor (e.g. 3–5 min) imaging resolution. While such resolution may be sufficient where images of large objects are to be generated, much higher resolution (e.g. 500 microns or below) is required when small animals (e.g. a mouse) or a limited region of interest in humans is to be examined.

Although imaging of radiotracers labeled with positron emitting radionuclides is extremely useful, positron emitters tend to have short half lives (e.g., C-11 (20 seconds), O–15 (2 minutes), F-18 (2 hours)). This makes such radiotracers unsuitable for studies in which the specific radiopharmaceutical is known to take several days to concentrate in the organ of interest. Furthermore, some compounds of biological interest may not be readily labeled with available positron-emitting nuclides, or the resulting radiopharmaceutical may possess undesirable biochemical characteristics. It is also the case that short lived positron emitters must be produced on site, and this often requires an expensive cyclotron installation and radiopharmaceutical preparation facility.

PET imaging also has other inherent shortcomings. First, PET imaging depends upon detection of both photons from a single annihilation event and therefore depends upon the entire path length through any intermediate attenuator (e.g., the mass of a patient between an annihilation location and the detector). In fact, it has been observed that attenuation in PET coincidence mode at 511 keV for a source at the center of an object is always greater than the attenuation of even 90 keV photons in a single photon counting mode. This severe attenuation results in few photons detected from "deep" structures in PET.

Second, in volume PET imaging, sensitivity decreases significantly toward the edges of the axial field-of-view with the joint angle "seen" by the annihilation radiation. In other words, often one annihilation photon in a pair may be detected while the other photon in the pair shoots axially out of an imaging area and is never detected.

Third, even where an annihilation pair reaches opposing PET detector sections, often only one of the two photons will be detected, the other of the two photons passing through the absorption member without an absorption event.

Fourth, where more than two absorption events are simultaneously detected with a conventional PET system there is no good way to determine which of the multiple events are associated with a single annihilation and hence there is no way to determine the sources of the photons. In effect, the data is lost.

Collimated Single Photon Camera

There are many radionuclides which emit one or more photons which are not correlated in angle as are the annihilation photons related to positron emitters. These are known as single photon emitters. Single photon emitters are readily available with a wide range of chemical properties, photon energies and half-lives. Single photon emitters cannot be imaged using coincidence techniques in the same manner as positron emitters.

Another imaging system which relies on detection of emissions and can detect single photons is a mechanically collimated emission camera. A collimated camera is similar to the construction of a single PET camera in that this type of camera includes some type of absorption member which is capable of sensing a photon's absorption energy and location. To determine the angle of photon flight prior to absorption a collimated camera includes a collimator which essentially restricts absorbed photons to known paths which are often perpendicular to a broad face of the absorption member. While a collimated camera reduces the amount of calculations required to identify the source of a detected photon, collimated cameras have extremely low sensitivity and resolution is negatively affected by the collimator.

Compton Camera Imaging

An exemplary Compton camera includes first and second detectors which are both arranged to one side of an imaging area and the position of the second detector with respect to the first is locked and known. The first detector is designed to cause a photon to Compton scatter (i.e., a scattering event) within a scattering member so that photons emanate from the first detector along modified trajectories and having modified energies. The first detector senses the position of the scattering event, the energy absorbed during the scattering event and the time of the scattering event. To this end the first detector is typically relatively thin so that the number of photons which are completely absorbed within the first detector is relatively small. Related effects of a thin detector include reduced interactions after a first interaction and a smaller range of depth-of-interaction variances.

The second detector is configured and positioned such that the detector is within a path likely to be traversed by scattered photons. To this end, as scattered photons may scatter in virtually any direction, most second Compton camera detectors define a space in which the first detector is positioned. For instance, an exemplary second detector may have the shape of a box with an open face, the first detector being positioned within the open face so that any photon which scatters from the first detector into the box, despite the angle of scatter, will be detected by the second detector.

An absorption member within the second detector absorbs the scattered photons (i.e., an absorption event), identifies the positions of the absorption events, the energies absorbed during the absorption events and the times of the absorption events. The energies and locations of coincident scattering and absorption events are combined with a knowledge of the expected energy of photons generated by the imaging radionuclide to identify, within a conical ambiguity, the possible paths of a corresponding photon prior to collision with the first detector.

After conical data corresponding to a large number of detected photons has been generated, tomographic techniques are employed to locate the origin of the photons by finding the intersections of many different possible path cones corresponding to different detected photons. As in the case of PET, the source data is then combined to generate an image of the object of interest.

The quality of images generated using a Compton camera, like the quality using a PET system, is degraded by both multiple Compton scattering and depth-of-interaction variances in the second detector. In fact, Compton camera systems which depend upon scintillation detectors for the second detector have even a worse problem with uncertainty in the first detector interaction point than conventional PET cameras. In addition, such Compton cameras also generally have lower sensitivity than PET cameras.

Moreover, Compton cameras also have a number of additional shortcomings. Specifically, Compton cameras require extremely accurate first and second detectors, each of which can provide accurate event times, energies and locations. In the case of the first detector, required accuracy is not particularly burdensome as the area of the first detector is relatively small and hence the cost of configuring an accurate detector is practical. However, in the case of the second detector, the area of the second detector is relatively large (i.e., the entire internal surface of a box shaped detector) and hence the associated costs are appreciable.

Second, the processor required to resolve the conical ambiguities among many different valid events has to be extremely computationally capable. Such processors are relatively extensive when compared to the processors required to manipulate PET data.

In addition to the problems discussed above, radionuclide imaging generally has a number of other shortcomings. First, as well known in the imaging art, image quality can be increased by reducing the distance between a photon source and a detector. For instance, in the case of a Compton camera, the closer the first detector is to the object of interest, the smaller the spatial uncertainty corresponding to a given angular uncertainty. Moreover, being close to the object of interest increases the solid angle subtended by the first detector from the point of interest and camera sensitivity increases correspondingly. For this reason Compton cameras are typically mounted on multi-articulate arms which can position the first detector adjacent the object of interest. Unfortunately, because the arm must support each of the first and second detectors, the arm must be relatively large and often complicated. In addition, even with a suitable arm, often the external surface of the object of interest or the body in which the object resides is much different than the surface of the first detector so that distances between the object of interest and the first detector are appreciable.

Second, often, in addition to being absorbed by an object of interest, a radiopharmaceutical will be absorbed by other tissues or organs which are not of interest but which are proximate the organ of interest. In this case it may be difficult to differentiate between photons emanating from the organ of interest and photons emanating from surrounding tissue or organs. One solution may be to block photons from surrounding tissue and organs using radio-opaque shielding (e.g., a lead shield) or a collimator. Unfortunately, in cases where there is some distance between the organ of interest and the first detector, a blocking shield is relatively ineffective as photons from the tissue and organs adjacent the organ of interest can impact the first detector on an angle. In addition, where the organ of interest is not proximate the first detector, an effective collimator which could block angled photons from the tissue and the organ of interest would have to have extremely small apertures. Such a collimator would substantially reduce the sensitivity of a Compton camera thereby minimizing one of the advantages typically associated with Compton systems.

Because there are several shortcomings and advantages associated with each of the systems described above, it is advantageous for any medical or other type of facility which employs emission imaging systems to have one of each imaging system. Unfortunately, each imaging system is extremely expensive and therefore most facilities have been forced to chose one system and its advantages and shortcomings over the other systems.

One solution which has enabled both PET and single emission imaging using a single system includes two collimated single emission cameras including a coincidence processor. Each of the cameras can be used separately for single emission imaging. In the alternative, the cameras can be arranged so as to oppose each other, can be linked to the coincidence processor and the collimators can be removed so that a PET system is configured. No similar "double duty" system has been provided for PET and Compton imaging.

A need exists for a PET imaging system which is extremely accurate when a radiopharmaceutical which generates high energy photons is used to generate imaging data. In addition, it is always advantageous to have a Compton camera which includes a first detector which is as close as possible to an object of interest and therefore any Compton camera configuration which can reduce the distance between an object of interest and a first detector would be a welcome development. Moreover, an imaging system which could facilitate both Compton and PET imaging and which could increase imaging sensitivity at minimal expense would be particularly advantageous.

BRIEF SUMMARY OF THE INVENTION

In emission imaging systems photons which emanate from a radionuclide concentrated within an object of interest are detected and used to generate an image of the object. To this end two important detected photon characteristics must be determined for the detected photon to be useful for imaging purposes. First, the photon energy must be determined and compared to the expected energy of photons generated by the imaging radionuclide. Where a photon is not within the expected range either the photon is from a source other than the radionuclide in the object or the photon's energy was reduced by some interaction (e.g., collision with other matter in the patient's body or within an imaging vicinity) which likely changed the photon trajectory prior to detection. In either of these cases, the photon should not be used for imaging and should be discarded. Second, for photons within the expected energy range, the photon path must be determined so that the path can be traced back to the photon source.

As indicated above, upon a first interaction within an absorption member high energy photons deposit some energy and then tend to Compton scatter in a random direction. Nevertheless, if a single scattering event occurs at an event location and then the scattered photon exits the detector, the event location is accurate.

By providing opposing detectors on opposite sides of an imaging area, each of which causes a scattering event when two photons from a single annihilation are detected, as with any PET imaging system, the location of the annihilation and hence the location of the photon source can be determined as being along a line between the two scattering event locations.

Unfortunately, because the scattering detector scatters photons, there is no way, with the scattering detectors alone, to determine the total energy of the sensed photon. For this reason, with the scattering detectors, there is no way to determine if the photon is from the imaging radionuclide or whether the photon changed trajectory after the annihilation.

According to the present invention a second detector can be provided for each first detector wherein the second detector is designed to totally absorb scattered photons thereby determining the residual energy of each scattered photon. Thereafter, the scattering event energy and the residual or absorption energy can be combined to determine the total or sensed energy corresponding to the detected photon. Then, the sensed energy can be used to determine if the sensed photon corresponds to a valid event (i.e., has an energy within the expected energy range given the imaging radionuclide).

Thus, by providing opposing cameras wherein each camera includes a scattering detector and an absorbing detector, scattering and absorption energies can be combined to identify valid sensed events and then coincident scattering event locations for valid events in the opposing detectors can be identified for determining photon source location and for additional imaging purposes.

Thus, one object of the invention is to provide a relatively inexpensive imaging system. To this end, the second detector in each camera need not identify absorption event location. In addition, conventional PET processing as opposed to Compton type processing can be used to determine photon source location.

Another object is to provide an imaging system which can be used with high energy photons. The inventive system works best with high energy photons which are more likely to Compton scatter than to be absorbed upon an interaction with the first detectors.

One other object is to reduce the adverse effects of depth-of-interaction variances. To this end, the first detector in each camera is designed such that the detector can provide an accurate three dimensional scattering location for each scattering event.

Consistent with the objects of the invention, an exemplary embodiment of the invention includes an apparatus for identifying the location of a photon source within an imaging area and which generates photons having energies within a known energy range. The apparatus including two oppositely facing detector pairs or cameras disposed on opposite sides of the imaging area, each camera including a first detector unit which causes Compton scattering when a photon enters the unit and generates signals indicative of the scattering event location, energy and time and a second detector unit which absorbs the scattered photon and generates signals indicative of the absorption event energy and time. Where combined coincident scattering and absorption event energies detected by a camera are within the expected energy range, the scattering event location is identified as the location of a valid event. Thereafter, the times of valid events in each of the opposing cameras are compared and the event locations corresponding to coincident valid events are identified and stored as coincident event pairs. The coincident event pairs can be used to identify the location of the photon source and also can be used subsequently for imaging purposes. The invention also includes a method to be used with the inventive apparatus.

Yet another object of the invention is to provide a Compton camera wherein the first detector can be as close as possible to an object of interest which is to be imaged. To this end, it has been recognized that the first detector in a Compton camera can be very compact and light weight as a Compton camera does not require a bulky mechanical collimator. In addition, it has been recognized that there is substantial leeway in the location of the second detector in the Compton camera. These two factors make it possible to design special purpose imaging geometries where the first detector can be placed very close to the regional anatomy (e.g., breast, prostate, extremity) being imaged, and can be shaped to conform to a patient's anatomy. Specifically, the first detector can take any desired shape and be placed within a conventional "imaging area" while the second detector(s) can be positioned outside the imaging area.

One other object is to provide a system where the relative positions of the first and second detectors in a Compton camera can be modified while still enabling collection of data meaningful for imaging purposes. To this end, in one embodiment the invention includes a relative position determiner which determines the relative positions of the first and second detectors and the relative position information is then used, along with conventional Compton camera data, to determine photon sources and generate suitable images.

One other object of the invention is to provide a "Compton probe" which can be used to locate radionuclides and hence tissue and organs which absorb radionuclides within a patient. After removal of a tumor, often residual tumorous tissue may remain. Compton imaging can be used for locating the residual tissue but going in and actually identifying the tissue for retrieval purposes is often a difficult task. According to the invention a small Compton camera is positioned at a distal end of a probe member, the camera including an entrance window which leads into a first detector and then to a second detector. The camera is linked to a processor which receives first and second detector data and can use the data to generate an image of the area in front of the window. To correlate the imaging data as the probe member is moved about, the probe member includes an orientation tracking device which determines the position and orientation of the camera in real time. The processor is linked to a display for displaying an image of the area adjacent the probe window. In effect, a probe user can "paint" a picture of the area adjacent the window by moving the distal end of the probe about proximate a photon source.

One other object is to identify proximity of the inventive probe member to tumorous tissue. As indicated above, positrons only travel a very short distance prior to annihilation. Thus, by providing a positron sensor within the window of the Compton camera at the end of the probe member, when positrons are sensed, tumorous tissue (i.e., tissue with a radionuclide absorbed therein) is located.

Yet another object is to provide a collimator on a first Compton detector which can block photons from tissue and organs which are not of interest but which only minimally reduces camera sensitivity with respect of an object of interest. To this end, it has been recognized that by providing first detectors which are anatomically shaped and therefore can be positioned extremely close to an organ of interest, the fields of view for viewing an organ of interest can be reduced appreciably using shielding or a collimator with minimal sensitivity reduction to photons emanating from the organ of interest.

One other object of the invention is to provide a relatively inexpensive "multi-purpose" imaging system which can be used for Compton imaging and PET imaging or can be used in a dual mode wherein both Compton and PET features are combined to increase both sensitivity and source resolution.

To this end, it has been recognized that the second detector in a conventional Compton camera is structurally and functionally very similar to detectors used for PET imaging. Thus, in addition to being used for PET imaging, a PET camera can also be used in conjunction with a scattering Compton detector to facilitate Compton imaging wherein the additional hardware expense for Compton imaging is only the expense of the scattering detector.

Furthermore, it has been recognized that in addition to facilitating both Compton and PET imaging/processing, a system including scattering detectors and PET type second detectors arranged in an opposing PET formation can be used to increase sensitivity and resolution. To this end, it has been recognized that a PET system including scattering first detectors can result in three different types of "useful" detected events. The three types of events include conventional PET coincidences where a pair of photons corresponding to a single annihilation event are detected in the PET detector, a single Compton event where one photon corresponding to an annihilation pair escapes detection and the other photon in the pair interacts by Compton scattering in the first detector and absorption in time-coincidence in the second detector and mixed events where the two annihilation photons (which may correspond to either one or two annihilations) have been detected and additionally, one or both photons have scattered in the first detector and are detected in the second detector.

With respect to PET coincidences, these events are processed according to conventional PET techniques to identify source along a line segment connecting the locations of the two interactions. With respect to single photon Compton events, these events are processed according to conventional Compton techniques. With respect to mixed events, these events are processed in any of several different ways depending upon the nature of the detected events. For example, if two Compton scatters corresponding to a single annihilation occur and each scattered photon is absorbed in the second detector, the Compton position information is used in a PET fashion to identify source location. As another example, Compton data can be used to indicate whether a recorded event is a random coincidence or not. For instance, assume each photon in an annihilation pair Compton scatters but only a single scattered photon is absorbed in the second detector. In this case, coincidence can be used to determine that it is likely that the scattered photons form a pair but the energy of the unabsorbed photon cannot be determined because that photon was not absorbed. Compton processing can be applied to scattering and absorption data corresponding to the absorbed photon to identify the source of the absorbed photon within a conical ambiguity. Once the cone of possible photon trajectories is known, if the line between the scattering events is on the cone, it can be assumed the scattering photon which was not absorbed is not a random coincidence and therefore the photon source, along a line, can be determined. Where two coincident events are not from a single annihilation, the events can be Compton processed separately.

A similar procedure can be used to determine if an annihilation photon scattered prior to detection. For example, assume annihilation photons both scatter and are absorbed. In this case a line between scattering event locations identifies a likely source location. To verify source location, Compton processing can be performed on scattering and absorption data corresponding to a single one of the photons to identify source within a conical ambiguity. If the line between scattering events is not on the identified cone, the events are random coincidences.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DETAILED DESCRIPTION OF THE INVENTION

A. Hardware Configuration

Figure 2:
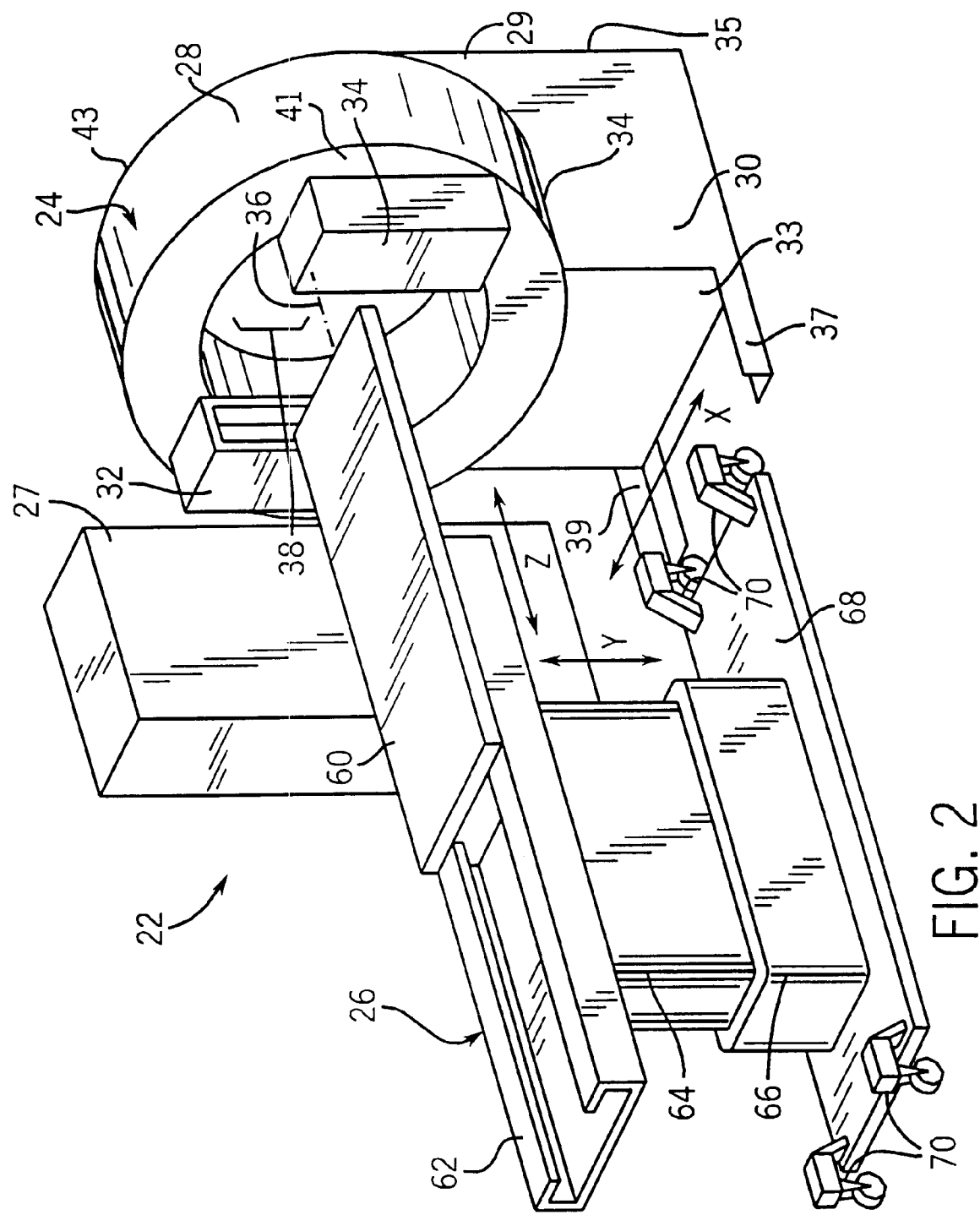
FIG. 2 is a perspective view of an exemplary PET imaging system embodying the present invention.

Referring now to the drawings, wherein like reference numerals represent corresponding elements throughout the several views, and more specifically, referring to FIG. 2, there is shown, generally at 22, imaging hardware including a PET imaging system 24, a patient support table 26 and a processor 27.

Support table 26 includes a top surface 60 interleaved to a lower bracket member 62 which allows supported movement of the top surface 60 along a horizontal Z-axis. The bracket member 62 is supported by a vertical leg 64 which extends upwardly from a collar 66. The length of leg 64 can be increased or decreased to raise or lower top surface 60 along a vertical Y-axis. Collar 66 is secured to a planar dolly 68 having four wheels collectively identified by the numeral 70, one wheel 70 attached at each of four corners. The wheels 70 allow an operator to move the entire table 26 laterally along an X-axis or along the Z-axis. Thus, the table 26 allows an operator to move the top surface 60 and a patient thereon within a range of three dimensional space.

System 24 includes a pedestal 30, a gantry 28 and two planar imaging cameras 32, 34. Pedestal 30 has a front end 33 and a back end 35 and includes two stabilizing legs 37, 39 which extend forward from the front end 33, distal ends of the legs 37, 39 contacting a ground surface in front of the pedestal to stabilize the pedestal front end 33 as system 24 is generally front end heavy. The top surface of pedestal 30 is generally shaped concavely upward so as to receive an outer surface of gantry 28. In addition, although not shown, pedestal 30 may also house a gantry motor for rotating gantry 28 about a central gantry rotation axis 36.

Gantry 28 is generally doughnut shaped about the central rotation axis 36. The pedestal 30 supports the gantry 28 in an upright vertical orientation so that its rotation axis 36 is horizontal and can be parallel to the support table Z-axis. Gantry 28, like pedestal 30, has a front end and a back end defined by front and back surface 41 and 43, respectively. The gantry 28 ideally can rotate about central rotation axis 36 through a complete rotation and, at a minimum, to produce 360° imaging, must be able to rotate through 180°.

Cameras 32 and 34 are mounted securely to gantry front surface 41 so that when gantry 28 rotates about axis 36, the cameras 32, 34 likewise rotate. Cameras 32 and 34 are mounted so as to directly oppose each other on opposite sides of an imaging area 38 therebetween. Cameras 32 and 34 are used to detect and identify the coordinates of a source of photons which resides within imaging area 38. To this end, each camera 32 and 34 is linked to processor 27 via a bus (not illustrated in FIG. 2) and provide position, energy and timing information to processor 27 corresponding to sensed events where an event is a sensed photon. Cameras 32 and 34 are essentially identical in construction and operation and therefore, in the interest of simplifying this explanation, unless indicated otherwise, only camera 32 will be explained in detail.

Figure 1:
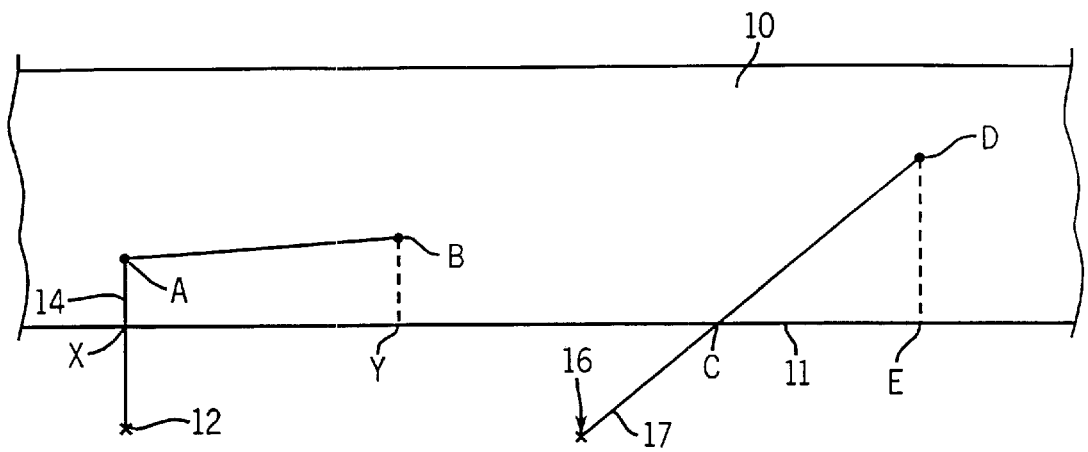
FIG. 1 is cross-sectional view of a two event photon absorption and the effects depth-of-interaction variances in a detector.
Figure 3:
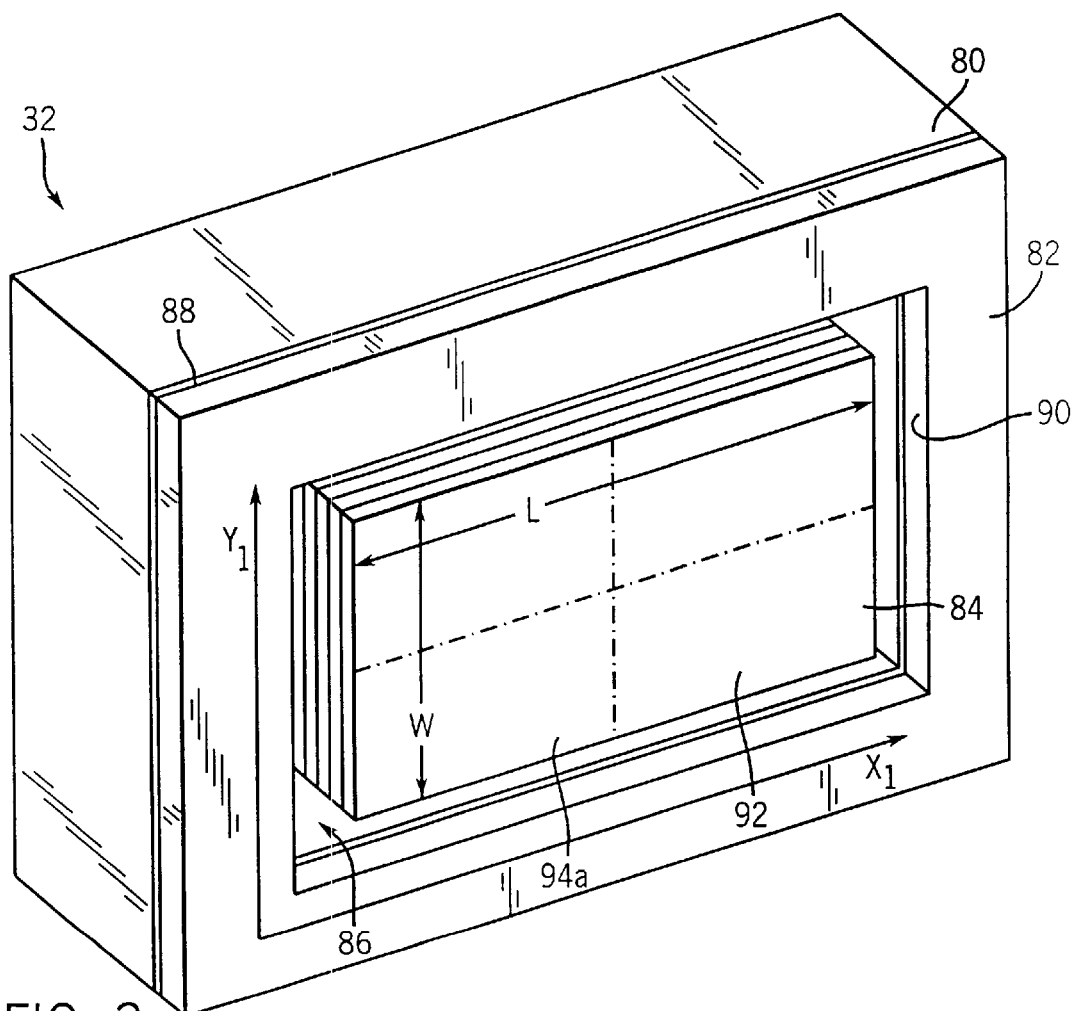
FIG. 3 is a perspective view of a camera according to the present invention.
Figure 4:
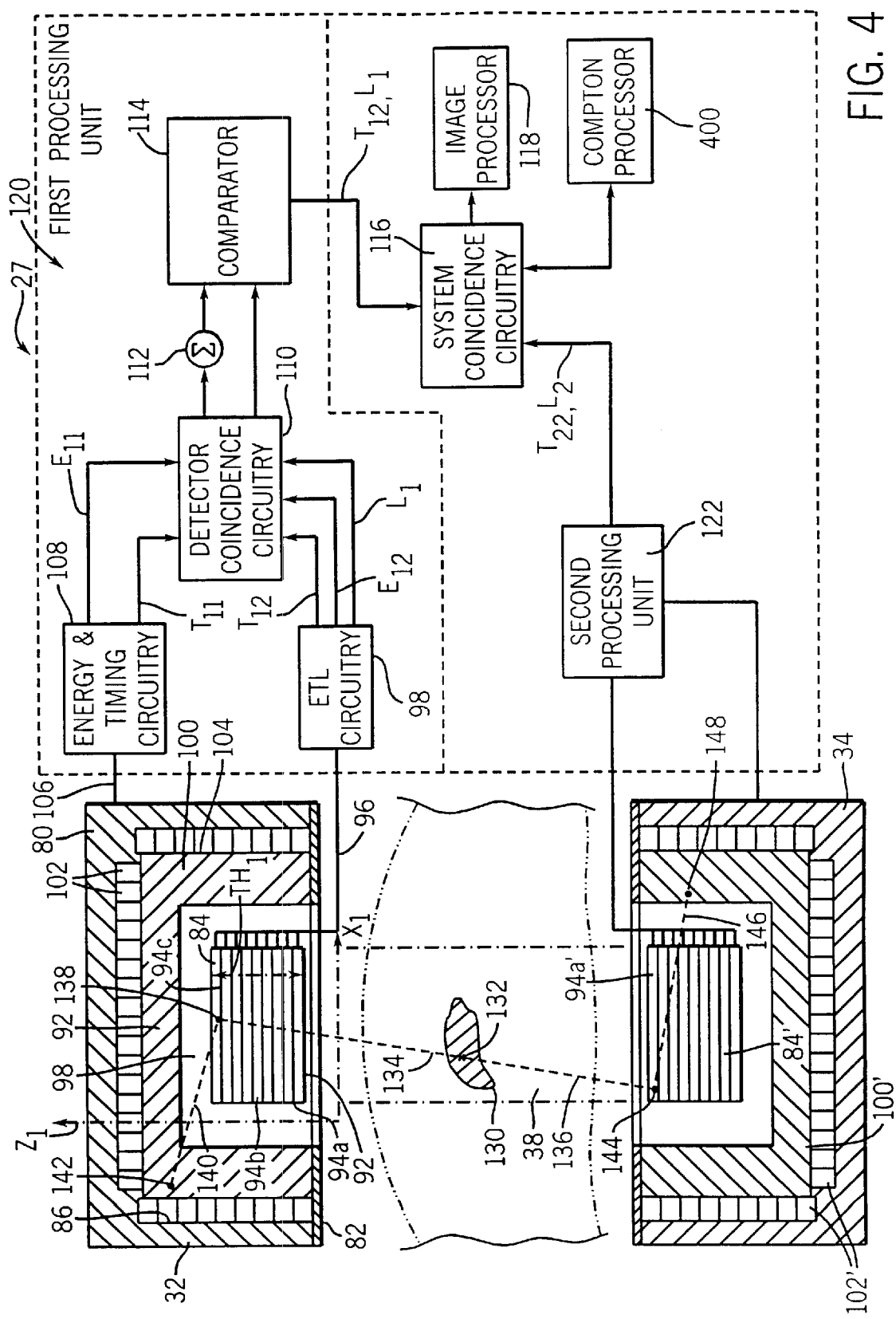
FIG. 4 is a schematic diagram of an imaging system including the camera of FIG. 3.

Referring now to FIGS. 3 and 4, exemplary camera 32 generally includes a radiation attenuating boot 80, a radiation attenuating frame member 82, a first detector unit 84 and a second detector unit 92. Boot 80 is essentially a box forming a cavity 86 and having an open face 88. Boot 80 is formed of a radiation attenuating material such as lead which blocks or absorbs radiation. Detector unit 92 is shaped like boot 80 but is dimensioned such that unit 92 fits within cavity 86 and forms an inner cavity 98. To this end, exemplary unit 92 is a scintillation type camera including a scintillation crystal 100 and a plurality of photo-multiplier tubes (PMTs), two of which are collectively referred to by numeral 102. PMTs 102 line the entire internal surface of boot 80. Crystal 100 includes a plurality of walls which form an opened faced box between PMTs 102 and inner cavity 98.

Construction and operation of scintillation type detectors are well known in the imaging industry and therefore will not be described here in detail. Nevertheless, certain characteristics of detector unit 92 are important for the purposes of the present invention and should be noted. First, the shape of second detector unit 92 is configured so as to surround first detector unit 84 so that most photons which are Compton scattered within first detector unit 84 travel into some portion of scintillation crystal 100. Second, scintillation crystal 100 is relatively thick to ensure that virtually every photon entering crystal 100 is fully absorbed within crystal 100 either upon a first interaction or, if addition Compton scattering occurs within crystal 100, upon subsequent interactions within crystal 100. Third, each interaction within crystal 100 generates light in proportion to the energy which is deposited within the crystal 100 by the interacting photon. Fourth, PMTs 102 are linked via bus 106 to energy and timing circuitry 108 in processor 27. Fifth, when PMTs 102 detect light from a photon interaction or a plurality of interactions corresponding to a single photon, PMTs 102 provide signals to circuitry 108 which can be used by circuitry 108 to determine both the time of the interaction or interactions within crystal 100 and the amount of energy deposited within crystal 100.

Detector unit 84 is mounted within inner cavity 98 and defines a planar surface 92 having a width W and a length L along $Y_1$ and $X_1$ axes, respectively. When mounted within cavity 98, planar surface 92 is positioned within cavity 98 and adjacent and parallel to a plane defined by open face 88.

Detector unit 84 is formed of a plurality of solid state planer detectors which are stacked so that each detector is parallel to the plane defined by the $X_1$ and $Y_1$ coordinates. In the Figures, unit 84 is illustrated as having nine separate solid state detectors, three of which are identified by numerals 94a, 94b and 94c, respectively. Solid state detectors are well known in the imaging arts and therefore construction and operation details of solid state detectors will not be described here in detail. To gain a better understanding of construction and operation of a solid state detector, reference may be had to exemplary detectors described in U.S. Pat. No. 5,198,673 entitled "Radiation Image Detector With Optical Gain Selenium Photo-Sensors" which issued on Mar. 30, 1993 or U.S. Pat. No. 5,677,539 entitled "Semiconductor Radiation Detector With Enhanced Charge Collection" which issued on Oct. 14, 1997, each of which is incorporated herein by reference.

While construction and operation of detectors 94a through 94c will not be described herein detail, an number of characteristics of solid state detectors 94a through 94c are important to operation of the present invention and therefore will be described. First, referring still to FIGS. 3 and 4, each of detectors 94a through 94c has a length L and width W dimension and the length and width dimensions are substantially greater than a thickness dimension corresponding to the specific detector. In fact, the thickness of each detector 94a through 94c should be extremely minimal to reduce the effects of depth interaction variances. Second, each detector 94a through 94c is designed to maximize the probability of a Compton scatter when a photon enters an absorption member of the detector and to minimize the probability of absorption within the member. The scattering results in an energy deposition within the detector at the scattering event location and alters the trajectory of the scattered photon. Third, each detector 94a through 94c is linked via a bus 96 to energy, timing and location (ETL) circuitry 98 in processor 27. Fourth, each detector 94a through 94c is capable of generating signals, upon the occurrence of a Compton scattering event, which can be used by ETL circuitry 98 to determine the deposition energy level within the detector, the time of the scattering event and the $X_1$ and $Y_1$ coordinates of the scattering event.

When stacked as illustrated, detectors 94a through 94c form detector unit 84 having a thickness $Th_1$ along a $Z_1$ axis which extends into cavity 86 and which is perpendicular to each of axes $X_1$ and $Y_1$. Frame member 82, like boot 80, is formed of an attenuating material such as lead which blocks photons. Member 82 is rectilinear, forms a large collimator aperture 90 and is dimensioned to fit on the open face 88 of boot 80.

Referring now to FIGS. 2 and 4, processor 27 includes first and second processing units 120 and 122, respectively, system coincidence circuitry 116 and an image processor 118. Units 120 and 122 correspond to first and second cameras 32, 34, respectively. Each of processing units 120 and 122 is essentially identical in construction and operation and, therefore, only unit 120 will be described here in detail. In addition to including energy and timing circuitry 108 and ETL circuitry 98, unit 120 also includes detector coincidence circuitry 110, a summing circuit 112 and a comparator 114.

ETL circuitry 98 receives signals from solid state detectors 94a through 94c and uses the received signals to determine three characteristics about each photon which causes a scattering event within detector unit 84. First, circuitry 98 determines the time at which a scattering event occurs and provides a time stamp $T_{12}$ for each scattering event. Second, circuitry 98 determines the total amount of energy deposited within unit 84 from a scattering event and provides an energy signal $E_{12}$ corresponding thereto. Third, circuitry 98 determines the location of each scattering event within the three-dimensions (i.e., $X_1$, $Y_1$ and $Z_1$) of unit 84. The three-dimensional interaction position or location is identified by reference symbol $L_1$ but includes each of an $X_1$ coordinate, a $Y_1$ coordinate and an indication of which detectors 94a through 94c detected the scattering event. In other words, the detector 94a through 94c is used as an indication of a $Z_1$ axis coordinate.

Energy and timing circuitry 108 receives signals from PMTs 102 corresponding to each absorption event within crystal 100 and uses the received signals to identify two absorption event characteristics. First, circuitry 108, like circuitry 98, determines absorption event time and provides a time stamp $T_{11}$ corresponding thereto. Second, circuitry 108 adds up all of the energy corresponding to an absorption event within crystal 100 and provides an energy signal $E_{11}$ corresponding thereto.

Referring still to FIG. 4, detector coincidence circuitry 110 receives first detector data packets including $T_{12}$, $E_{12}$ and $L_1$ signals and second detector data packets including $T_{11}$ and $E_{11}$ signals and stores those data packets in a buffer (not illustrated). Then, coincidence circuitry 110 compares time stamps $T_{11}$ and $T_{12}$ corresponding to stored data packets to identify each of a first and a second data packet which have essentially identical time stamps and therefore are caused by a single photon. When circuitry 110 identifies essentially identical time stamps $T_{11}$ and $T_{12}$, circuitry 110 provides corresponding data packet energies $E_{11}$ and $E_{12}$ to summing circuit 112 which sums the energy signals and provides a sensed photon energy signal to comparator 114. In addition, circuitry also provides position signal $L_1$ to comparator 114.

Comparator 114 buffers position signals $L_1$ and time stamps $T_{12}$ and compares the sensed energy signal to an expected energy range which corresponds a known energy level of photons generated by the imaging radionuclide. For example, where the radionuclide omits positrons, comparator 114 compares the sensed energy level to 511 keV or a small range there around to identify valid events. Where the sensed energy level is not within the expected range, comparator 114 discards the energy, time and location data related to the detected event. However, where the sensed energy level is within the expected range, comparator 114 provides the time stamp $T_{12}$ and scattering event location signal $L_1$ to system coincidence circuitry 116.

As indicated above, second processing unit 122 is essentially identical to first processing unit 120 except that unit 122 is linked to second camera 34. In operation, unit 122, like unit 120, provides time stamps and location signals to system coincidence circuitry 116 which correspond to valid events sensed by camera 34 wherein a valid event is a sensed photon which has an energy within the expected energy range. The time stamp and position signal provided by unit 122 are identified by symbols $T_{22}$ and $L_2$, respectively.

System coincidence circuitry 116 receives and buffers time stamps $T_{12}$ and corresponding location signals $L_1$ as first camera data packets and receives and buffers time stamps $T_{22}$ and corresponding location signals $L_2$ as second camera data packets. Thereafter, circuitry 116 compares time stamps $T_{12}$ of events detected by camera 32 to time stamps $T_{22}$ of events detected by camera 34. Where two time stamps $T_{12}$ and $T_{22}$ are essentially identical or are within a window calculated to indicate coincident events, circuitry 116 identifies corresponding locations $L_1$ and $L_2$ as a pair of locations related to a single annihilation event within an object to be imaged. Positions $L_1$ and $L_2$ are then provided to image processor 118 which stores the location pairs $L_1$ and $L_2$ as a coincident event pair for later image processing. Such additional processing is well known in the art.

B. In Operation

Referring still to FIGS. 2 and 4, in operation, a torso segment (shown in phantom) of a patient having an object of interest 130 is positioned on surface 60. Surface 60 is slid into imaging area 38 such that object 130 is positioned between planar surfaces (e.g., see 92 in FIGS. 3 and 4) and within imaging area 38. In the present example, it will be assumed that Fluorine-18 is the imaging radionuclide which generates photons having energies of 511 keV each.

After a radiopharmaceutical becomes concentrated within object 130, as the radionuclide within the radiopharmaceutical decays, subatomic particles (e.g., positrons) are released from the radionuclide and travel at high speeds within object 130 until they collide with electrons. Upon collision, the particles are annihilated. An exemplary annihilation is identified by point 132 in FIG. 4. Upon annihilation, a particle generates two photons (each having a 511 keV energy) which travel in opposite directions which, in FIG. 4, are identified by numerals 134 and 136 wherein path 134 defines a trajectory toward detector unit 84 and path 136 defines a trajectory toward a first detector unit 84' in camera 34.

Referring still to FIG. 4, as illustrated, when the photon traveling along path 134 reaches detector unit 84, the photon passes through the first eight solid state detectors without Compton scattering and finally scatters at a point 138 in ninth solid state detector 94c. Upon scattering at point 138 the photon deposits energy at point 138 and is scattered along a new trajectory 140 toward crystal 100. The scattered photon is absorbed in crystal 100 at point 142.

When the photon scatters at point 138, signals are provided to ETL circuitry 98 via bus 96. Circuitry 98 uses the received signals to generate each of time stamp $T_{12}$, energy signal $E_{12}$ and location signal $L_1$, all of which are provided to coincidence circuitry 110. Similarly, upon absorption at point 142, PMTs 102 provide signals to energy and timing circuitry 108 which uses the received signals to generate a time stamp $T_{11}$ and an energy signal $E_{11}$ corresponding to the absorption. Signals $T_{11}$ and $E_{11}$ are provided to coincidence circuitry 110. Circuitry 110 identifies coincident scattering and absorption events in first and second detector units 84, 92, respectively, and provides energies of coincident events to summing circuit 112. Summing circuit 112 provides a sensed photon energy level to comparator 114. Comparator 114 compares the total energy to the expected energy range and thereafter provides a first camera data packet including a time stamp $T_{12}$ and a corresponding position signal $L_1$ to coincidence circuitry 116 corresponding to each valid event (i.e. each photon having a sensed energy level within the expected energy range).

Similarly, referring still to FIG. 4, when the photon traveling along path 136 reaches detector unit 84', that photon Compton scatters within a first solid state detector 94a' at a point 144. Upon scattering, the photon deposits energy within detector 94a' and is scattered along a new trajectory identified by numeral 146, toward a scintillation crystal 100' in second camera 34. Within crystal 100', the photon is absorbed at a point 148 causing an absorption event.

Upon scattering at point 144, the photon deposits energy thereat which generates signals provided to second processing unit 122. Processing unit 122 determines the time of the scattering event, the three-dimensional location of the scattering event within unit 84' and the energy deposited within detector 94a'. At point 148, upon absorption, PMTs 102' in second camera 34 generate signals provided to processing unit 122. Unit 122 uses the absorption event signals to generate a time stamp corresponding to the absorption event and an energy signal corresponding to the absorption event. Thereafter, unit 122 identifies coincident second camera scattering and absorption events, adds up energies from coincident scattering and absorption events to generate a sensed photon energy level, compares the sensed level to the expected energy range to determine if the event is a valid event (i.e., the sensed energy level is within the expected energy range) and then provides second camera data packets including times $T_{11}$ and corresponding locations $L_2$ to circuitry 116.

Coincidence circuitry 116 compares time stamps $T_{12}$ and $T_{22}$ of first and second camera data packets and, where two time stamps are essentially identical, provides position signals $L_1$ and $L_2$ as a coincident event packet to processor 118. Processor 118 then uses the coincident event packet corresponding to all sensed photons to generate an image.

By combining scattering detector units and PET geometry, various unexpected advantages result. First, by using opposed detectors as is conventional in PET imaging, the location of a photon source can easily be determined once scattering event locations (e.g., 138 and 144 in FIG. 4) are identified by simply back projecting a line through the imaging area, the line passing through the annihilation point and hence the photon source 132. Second, because annihilation location 132 is easy to identify using scattering event locations, second camera unit 92 need not provide any location information corresponding to absorption event locations (e.g., 142, 148 in FIG. 4). Second units 92 must only provide signals for identifying absorption event time and accurate energy deposition within crystal 100. Thus, second detector units 92 can be relatively simple in design and relatively inexpensive. Third, by providing first detector units (e.g., 84, 84') which enable three-dimensional event location, the effects of depth-of-interaction variances are appreciably minimized.

C. Other Embodiments

Figure 5:
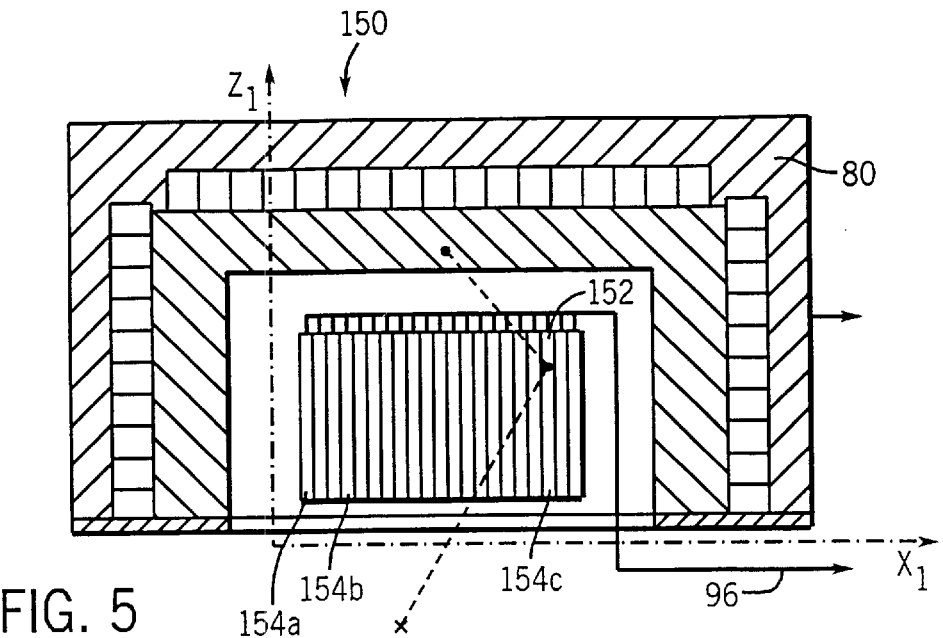
FIG. 5 is a cross-sectional view of a second embodiment of a camera according to the present invention.

It should be understood that the methods and apparatuses described above are only exemplary and do not limit the scope of the invention, and that various modifications could be made by those skilled in the art that would fall under the scope of the invention. For example, referring to FIG. 5, another inventive camera embodiment 150 is illustrated. Camera 150 is meant to be used in conjunction with a second camera (not illustrated) essentially identical to camera 150 which is placed in an opposing manner such that PET imaging can be performed with the two cameras. In addition, camera 150 and the opposing camera are linked to a processor like processor 27 described above.

Many of the components of camera 150 are identical or essentially identical to the components described above with respect to camera 32 and therefore, those component will not be described again here in detail. The primary distinction between cameras 150 and 32 is that a first detector unit 152 is designed differently than first detector unit 84. To this end, detector unit 152 includes a plurality of solid state detectors, three of which are identified by numerals 154a, 154b and 154c. Each of detectors 154a through 154c is essentially identical to the detectors 94a through 94c of camera 32, the distinction between unit 152 and unit 84 being that detectors 154a through 154c are stacked such that they are perpendicular to the plane defined by the boot open face 88. Thus, with camera 150, each of detectors 154a and 154c provides signals via a bus 96 which can be used to determine both a $Z_1$ axis coordinate and a $Y_1$ (i.e., into FIG. 5) coordinate and the $X_1$ coordinate is determined by which of detectors 154a through 154c generates scattering event signals.

In addition, referring again to FIG. 4, while solid state detectors 94a through 94c are illustrated as being stacked one on top of another, the invention contemplates cameras wherein small spaces are provided between adjacent solid state detectors for cooling purposes. Moreover, while it is desirable that each of the first detector units 84 and 84' in FIG. 4 consist of stacked solid state detectors, a relatively accurate two-dimensional detector unit may be used instead of the stacked detectors. While images will be slightly more blurred with this type of a design because Z-axis (i.e., depth) of event information is lost, advantages such as reduced cost second detector units still result.

It should also be noted that while the second detectors need not be position sensitive, the second detector may be position sensitive or at least partially position sensitive. Where the second detectors are position sensitive, photon pairs which are not scattered by the first detectors but which are absorbed by the second detectors can be used in a conventional PET manner to supplement data generated via scattered photons. Where the second detectors are at least partially position sensitive (i.e. are capable of roughly identifying absorption location), the rough position sensitivity can be used to select scattering events within the first detectors which may be related to specific absorption events thereby minimizing computing and data collection errors.

It is also possible that one of the annihilation photons interacts only in a second detector while the other scatters in a first detector and is absorbed in a corresponding second detector. This results in one high resolution determination of the trajectory paired with a low resolution determination. This information still represents a valid event and, given a specific algorithm, is still considered a useful event for imaging purposes.

For either annihilation photon in a related photon pair, if there is a Compton scatter in the first detector and the position of the interaction in the second detector is well known, then the scattering angle can be calculated as long as the photon trajectory can be established by a coincident detection of the second photon in the opposing PET detector. In this case, another estimate of the incident photon energy may be obtained that could be more accurate than that calculated from the second detector energy signal.

If two events are detected simultaneously (within a single coincidence window) in the first and second detector of a first PET/Compton camera, then knowing the position of the interaction in a second camera will help one to determine which first and second detector events should be paired. Consider that an unambiguous coincidence has occurred in an opposing second PET/Compton camera. One then has two possible photon trajectories to choose from. This ambiguity may be resolved in some cases by calculating the scattering angle from the energy deposited in each of the events in the second PET detector. Given the two events in the first detector, one can compute four possible cones. In many cases, only one of the two possible photon trajectories will lie on one of the conical surfaces (i.e., the conical surface will contain the first detector location on the opposing PET camera) and the ambiguity can be resolved.

There are two other event sequences which give good information on photon trajectory. The first sequence consists of either or both of the annihilation photons being absorbed in the first detector. If only one in a pair of annihilation photons is absorbed, the other photon may scatter and be absorbed in the second detector. Since the first detector is likely to have higher energy resolution than the second detector, absorptions in the first detector gives enhanced energy information. Position information is high resolution in either case.

A second class of sequences consists of events in which events that scatter in the first detector have secondary interactions in the first detector before being absorbed in either the first or second detectors. Since it is possible to determine the order of scattering events from the locations and deposited energies, one can determine which interaction occurred first and the photon trajectory information is high resolution.

Furthermore, the inventive PET/Compton system where the second (e.g., conventional PET detectors) detector is position sensitive can be used to identify photon source where an isotope which emits more than one photon is employed. For example, Indium-111 and Gallium-67 emit two or more "cascaded" photons at the same time. The source location of either of these cascade photons detected via a scattering event and an absorbing event can be localized to a conical surface. By detecting two of these photons in coincidence, the source is localized to the intersection of two cones. This localizes the source to a line in a three dimensional field of view. Similarly, if a third coincident photon is detected the conical surface related thereto can be used with the other two conical surfaces to locate the precise location of the source within the field of view.

Referring again to FIG. 4, where second detector units 92 are position sensitive, system 27 should also include a Compton processor 400 linked to system coincidence circuitry 116 to facilitate enhanced system operation. Hereinafter, the phrase "dual detected photon" will be used to refer to a photon which causes each of a scattering event and an absorption event and wherein the combined energies of the scattering and absorption events are within a known range corresponding to an expected photon energy and the phrase "single detected photon" will be used to refer to a photon which causes either a scattering event or an absorption event where the energy of the absorption event is within the known range.

When a dual detected photon is coincident with either one or more dual or single detected photons, the Compton processor 400 can be used to help identify photons related to a single annihilation event. For example, where two coincident dual detected photons are identified, conventional Compton type processing can be performed on absorption and scattering event data corresponding to one of the dual detected photons to identify possible pre-detection paths of the dual detected photon. Thereafter, processor 400 can verify that the scattering event associated with the coincident photon is path bound to one of the possible pre-detection paths.

As another example, where a first coincident photon is a single detected photon, and a second coincident photon is a dual detected photon, processor 400 can determine if the photons where from a single annihilation event by again determining the possible pre-detection paths of the dual detected photon and determining if the single detected photon is path bound. This is true whether or not the single detected photon was scattered or absorbed.

As yet another example, where even more than two detected photons are coincident and at least one of the photons is a dual detected photon, processor 400 can determine if one of the other detected photons is from the same annihilation as the dual detected photon by, once again, determining if the other detected photon scattering or absorption locations are path bound to a possible pre-detected path of the dual detected photon.

In one embodiment processor 27 is capable of simultaneously performing source location corresponding to a single dual detected photon, two dual detected photons, a dual detected photon and a single detected photon or a plurality of other detected photons, or two single detected and absorbed photons so that sensitivity and resolution are greatly improved.

Figure 6:
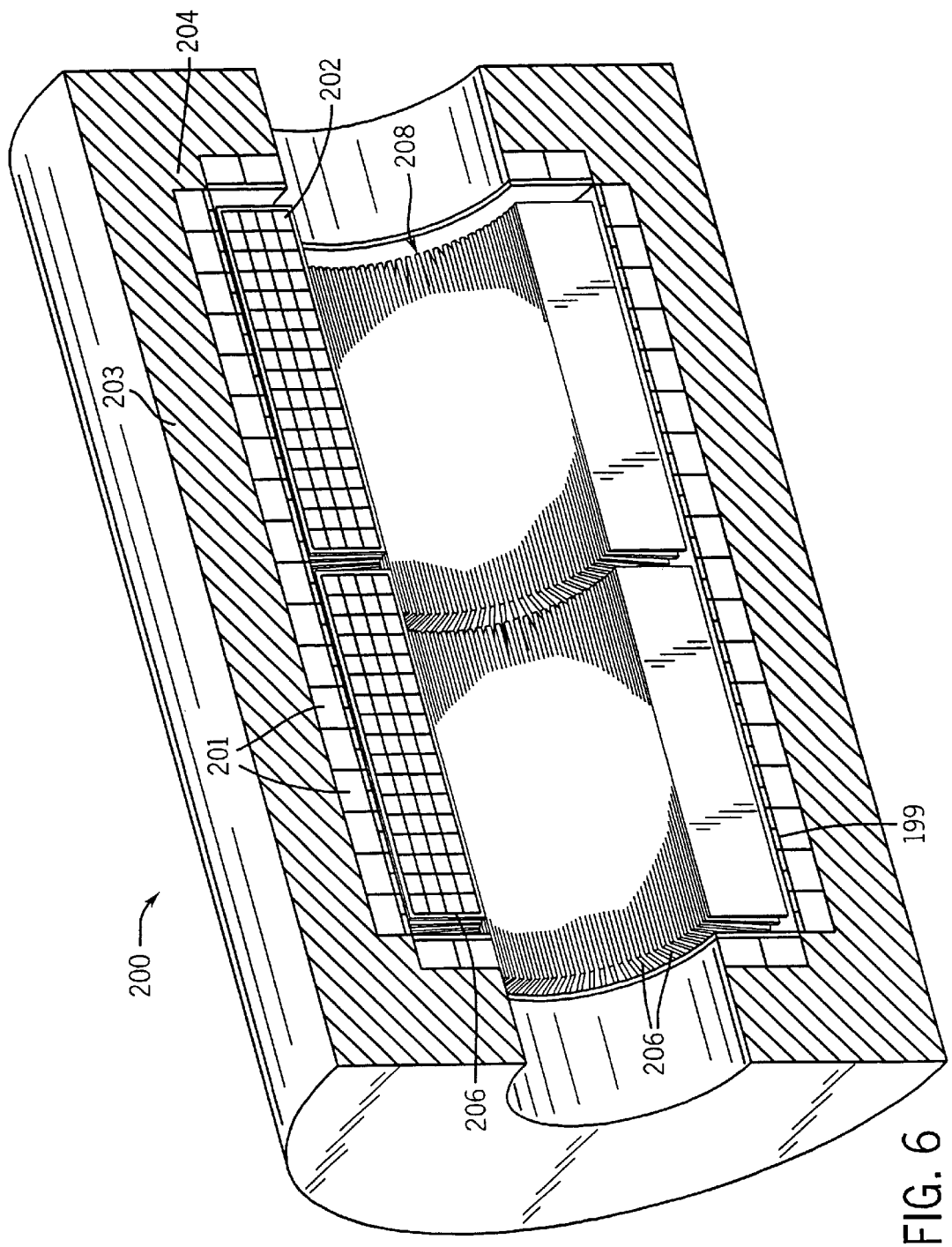
FIG. 6 is a cross-sectional view of a second inventive PET camera system.

Moreover, referring to FIG. 6, an annular embodiment 200 of the inventive PET system is illustrated in cross-section. Embodiment 200 includes a first detector 202 and a second detector 204. First detector 202 includes a plurality of solid state pixilated silicon detector elements, several of which are collectively identified by numeral 206. Elements 206 are arranged in a fan shape so as to form an annular imaging area or chamber 208. Elements 206 are each designed to have a high probability of scattering a photon and are capable of generating signals which can be used by a processor (not illustrated) to identify radial position and axial position. Circumferential position (i.e., the position about chamber 208) is determined by a processor (not illustrated) by identifying which of detector elements 206 causes a scatter. In addition to providing signals which can be used to identify the locations of scattering events, detector 202 also provides signals which can be used by the processor to identify scattering event times and energies.

Exemplary detector 204 includes a scintillation crystal 199, PMTs, several of which are collectively identified by numeral 201 which face detector 202 and radiation shielding 203 there around. As in the previous embodiments, detector 204 is only capable of identifying the energy levels of absorbed photons and the absorption times. Once again the processor receives signals from each of detectors 202 and 204, identifies coincident scattering and absorbing events having total energies which are within an expected range, the processor compares the scattering event times to identify coincident scattering times as coincident event pairs. An imaging processor (not illustrated) then uses coincident event pairs to generate an image.

Figure 7:
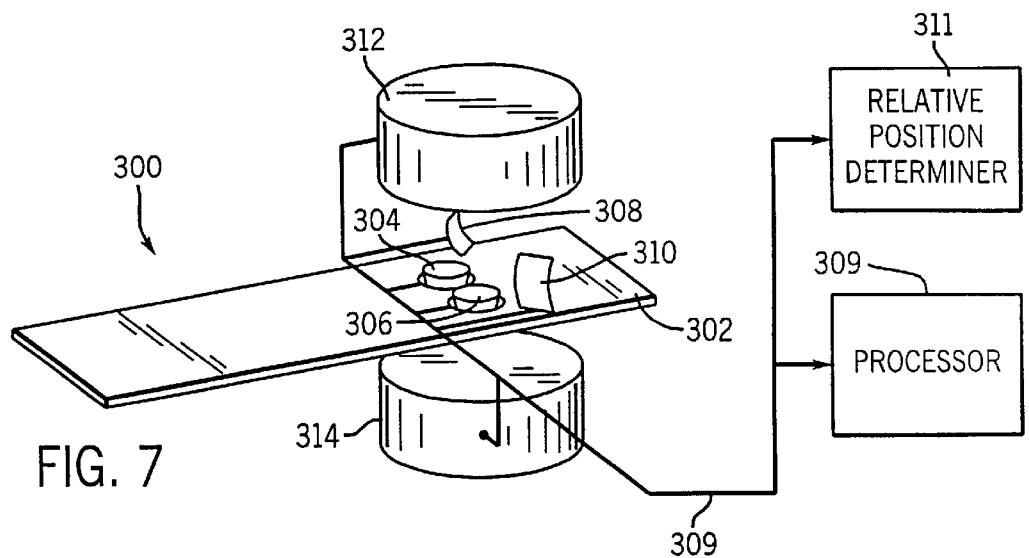
FIG. 7 is a schematic view illustrating one embodiment of an inventive Compton camera system.

Referring now to FIG. 7, in addition to the inventive PET systems described above, the invention also includes an inventive Compton camera system 300 which includes a support table 302, a plurality of first detectors, a plurality of second detectors, a relative position determiner 311 and a processor 309. The first detectors include first and second breast probes or detector units 304, 306, respectively, and two axillary node probes or detector units 308, 310, respectively. Detector units 304 and 306 are each in the form of tapered cups which are sized and juxtaposed such that they will receive typically sized and spaced breasts. Alternatively, the tapered cups might be split into halves and arrayed so that breasts might be imaged under moderate compression.

Detector units 308 and 310 are each "C" shaped arrays which are positioned such that they will be received adjacent a patient's armpits when the patient is placed in a prone position on support table 302. Each of probes 304, 306, 308 and 310 is preferably a multi-layered detector capable of identifying, along three dimensions, the location of a scattering event within the specific probe. In addition, each of probes 304, 306, 308 and 310 is constructed with a material and a geometry which increases the likelihood of a photon scattering within the detector (i.e., absorption of a photon within any of the probes is relatively unlikely).

Each of detector units 304, 306, 308 and 310 is capable of generating signals which are provided to processor 309 and which can be used by processor 309 to determine the location of, the time of and the energy deposited by a scattering event within the respective probe. In addition, each of units 304, 306, 308 and 310 provides signals to determiner 311 which determiner 311 uses to identify the precise position and orientation of the respective detectors 304, 306, 308 and 310.

In the exemplary system 300, second detectors include a first second detector 312 and a second to second detector 314. One choice for the second detectors is a pair of "SPECT-PET" cameras which may be operating in coincidence at relatively high count rates. In this example detectors 312 and 314 are positioned above and below support table 302 and data collected thereby is composed of events arriving in time coincidence between any of the first and either of the second detectors. Detectors 312 and 314 are linked to other system components via bus 309. Although not illustrated, other second detector geometries may be employed including a ring geometry or a "tire" geometry which surrounds a chamber in which support table 302 is inserted for imaging purposes.

Like the first detectors, each of detectors 312 and 314 is capable of generating signals which can be used by processor 309 to determine the location of, the time of and the energy deposited by an absorption event within the respective detector. In addition, each of units 312 and 314 provides signals to determiner 311 which determiner 311 uses to identify the precise position and orientation of the respective units 312 and 314. Determiner 311 also determines the precise relative positions between each first detector unit (e.g., 304, 308, etc.) and each second detector unit 312, 314 and provides relative position information to processor 309 for use in identifying the locations of photon sources.

Processor 309 uses the relative position information along with the event location, time and energy deposition signals from detector units 304, 206, 208, 310, 312 and 314 to determine the sources of sensed photons for imaging purposes.

While system 300 is illustrated as including an electronic determiner 311 for identifying the relative positions of first and second detectors, any mechanical, electronic or optical means could be used to identify the relative positions and the nature of the position sensing mechanism is unimportant. The important aspect with respect to determiner 311 is that some system is provided which can identify the relative positions of each first detector unit with respect to each second detector unit.

In operation, a patient is positioned in a prone position on support table 302 with her breasts in breast detector units 304 and 306 and her arms extended somewhat above her shoulders so that axillary detectors or probes 308 and 310 are positioned under her arms where they enclose axillary nodes on the left and right sides of the patient. Then, as photons emanate from radionuclides concentrated within the patient's breasts and axillary nodes, photons which emanate toward one of the first detectors 304, 306, 308 or 310 impact the detector and are scattered. Many of the scattered photons are directed in the direction of one of the second cameras 312 or 314. A scattered photon directed toward one of the second detector units 312 or 314 impacts the second unit and is absorbed thereby. Each of the scattering detector and the absorbing detector provides signals to processor 309 indicating location, time and deposited energy of the event sensed thereby. Thereafter processor 309 uses the received signals and relative position signals from determiner 311 to generate images of the objects which are being imaged.

Figure 8:
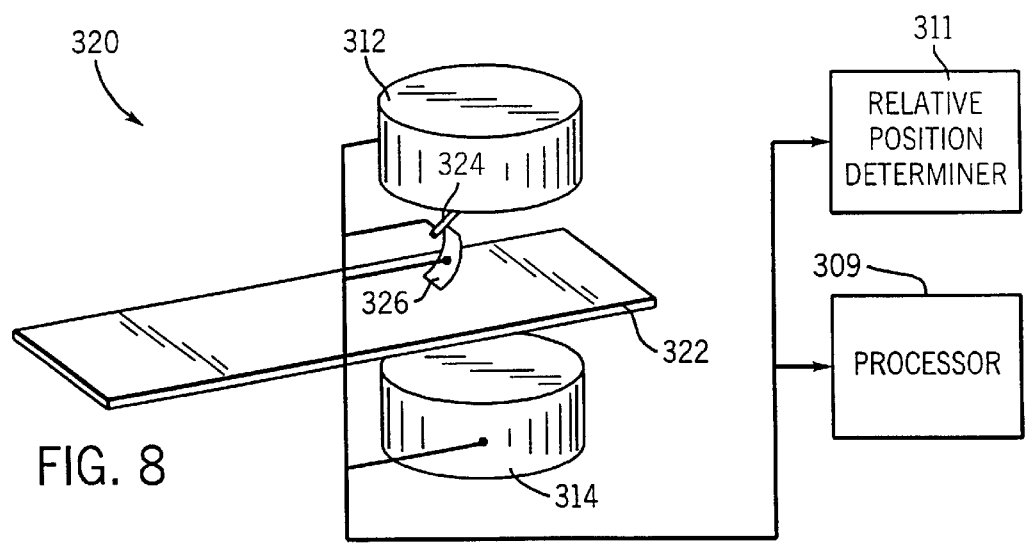
FIG. 8 is similar to FIG. 7, albeit of a second embodiment of an inventive Compton camera system.

Referring now to FIG. 8, another inventive system 320 according to the present invention is illustrated. System 320 is specifically designed for imaging a prostate and, to this end, includes a support table 322, first and second first detectors 324 and 326, first and second second detectors 312 and 314, respectively, a processor 309 and a relative position determiner 311. Processor 309, determiner 311, bus 313 and second detectors 312 and 314 are identical in form and function to similarly numbered components in FIG. 7 and therefore will not be explained here in detail. Suffice it to say that determiner 311 receives signals from each of detectors 324, 326, 312 and 314 and uses those signals to determine the relative positions of each of the first detectors 324 and 326 with respect to each of the second detectors 312 and 314 and provides relative position signals to processor 309 and that processor 309 receives signals from determiner 311 and from each of detectors 324, 326, 312 and 314 and uses all of those signals to determine the location of a photon source and thereafter to generate an image using data corresponding to a plurality of different photon sources.

Figure 9:
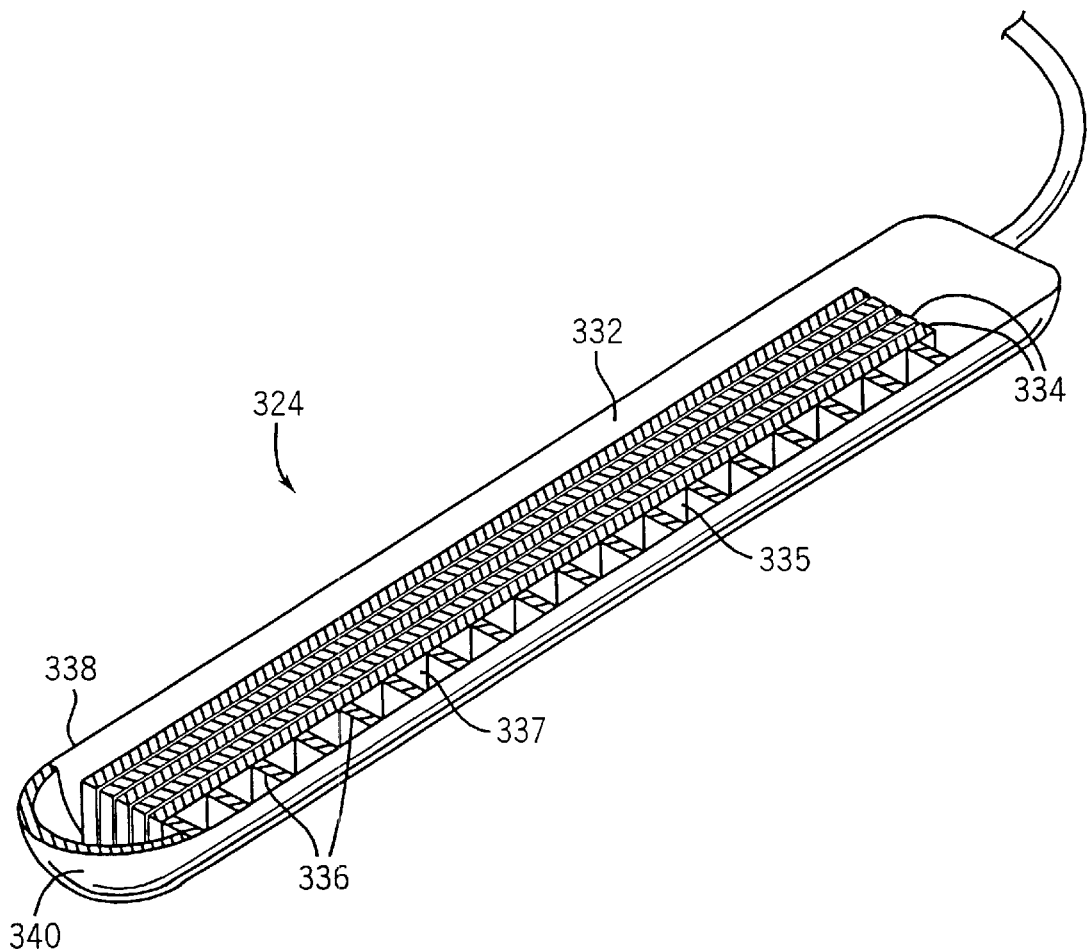
FIG. 9 is a cross-sectional view of the rectal probe of FIG. 8.

Referring also to FIG. 9, first detector 324 is in the form of a transrectal probe and to this end is formed of an elongated housing member 332 which houses a plurality of first detector elements, two of which are identified by a numeral 334, and a lead septa or collimator 336. Housing 332 is sized and shaped such that it can easily be inserted into a rectum. Elements 334 are stacked one on top of another with a broad surface 335 facing septa 336. Each element 334 is formed and constructed such that the probability of a photon scattering therein is relatively high when compared to absorption.

Septa 336 act as a collimator to block photons which emanate from a source which is not generally perpendicular with respect to the broad face of elements 334. Thus, a photon source positioned adjacent a distal end 338 of housing 332 will not generate photons which are sensed by elements 334. To further reduce the effects of such a distal source, a lead shielding dome 340 is provided at distal end 338.

Referring back to FIG. 8, preferably, detector 326, like all of the other first detectors described above, is also multi-layered so that it can generate signals which can be used to identify the location of a scattering event along three axis.

In operation, with a patient positioned in a prone position on support table 322, detector 324 is inserted within the rectum while detector 326 is placed adjacent a patent's groin. Then, as photons emanate from the prostate, photons directed toward either of first detector units 324 or 326 are scattered. A large number of the scattered photons are directed at one of the two second detector units 312, 314. Scattered photons directed at one of detector units 312 or 314 are absorbed thereby. Location, timing and energy deposition signals are provided to processor 309 which uses those signals to generate an image of the prostate.

It should be noted that the lead shielding and septa 340, 336, respectively, block radiation which may emanate from a source other than the prostate which is adjacent distal end 338. Preferably, septa 336 are relatively wide so that sensitivity is not appreciably reduced with respect to photons emanating from the prostate. Wide septa are possible because, in the present exemplary embodiment, detector elements 334 are extremely close to the prostate.

It should be appreciated that while specific shapes and detector configurations have been described above, many other shapes and configurations are contemplated. For example, while the inventive Compton cameras described above include two second detectors, some embodiments may only use a single second detector or may use an annular second detector to increase sensitivity. Similarly, while several first detectors are provided in each of the embodiments described above, the invention includes systems wherein there may only be a single first detector. Furthermore, it is contemplated that first and second detectors can be moved relative to one another and that additional first and second detectors can be added or swapped in and out of a system. In this regard, when detectors are added to a system determiner 311 has got to be equipped such that it can identify locations and relative positions with respect to the additional detectors.

Figure 10:
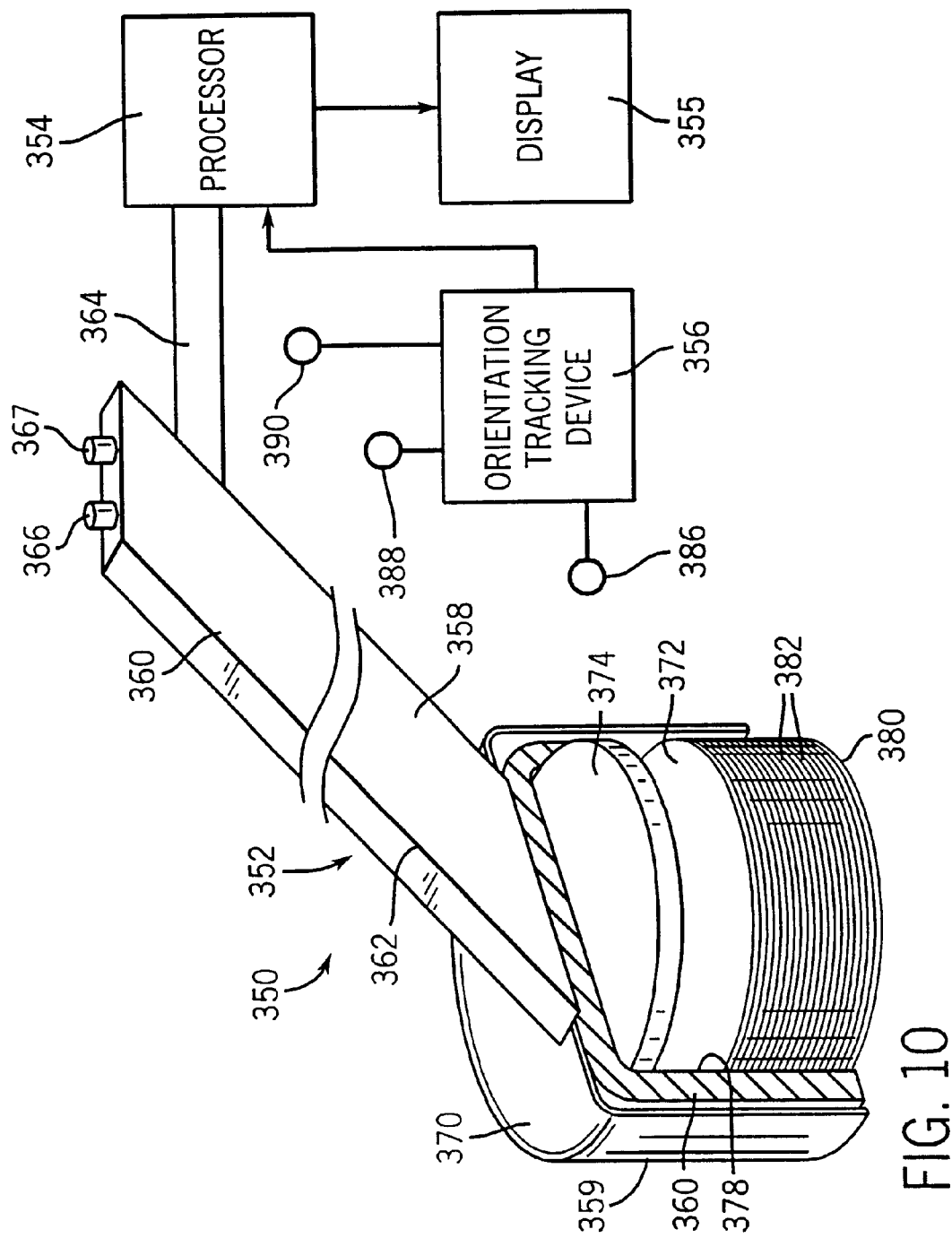
FIG. 10 is a schematic diagram of a Compton camera surgical probe according to e present invention.

Referring now to FIG. 10, yet another inventive system 350 is illustrated. System 350 includes a surgical probe 352, a processor 354, an orientation tracking device 356 and a display 355. Probe 352 includes a handle 358 and a Compton camera 359. Handle 358 includes a proximal end 360 and a distal end 362. Camera 359 is mounted to distal end 362. A data buss 364 links the proximal end (and camera 359 through handle 358) to processor 354. First and second transmitters 366 and 367 are mounted at proximal end 360 and are capable of sending infra-red or radio frequency signals. Transmitters 366 and 367 are rigidly mounted with respect to camera 359 such that the relative positions therebetween remain unchanged.

Camera 359 includes a cup shaped radio translucent housing 370, a first detector 372, a second detector 374 and a lead shielding member 376. Shield 376 is shaped like cup shaped housing 370 and fits therein, forming an annular chamber 378 which receives first and second detectors 372 and 374. Detector 372 includes a plurality of detector elements including a first element 380 and additional elements, three of which are collectively identified by numeral 382. Elements 380 and 382 are thin wafer-like members which have a circular general shape in the preferred embodiment. A thin radiotranslucent window is placed over element 380 to protect the probe from bodily fluids and to preserve sterility. Each of elements 380 and 382 is capable of sensing both positrons and photons. Elements 380 and 382 are stacked one on top of another to form detector 372. As with the preferred embodiments described above, each element 380 and 382 is designed such that when a photon enters the element, it is likely that the element will scatter the photon (i.e., absorption is relatively unlikely).

Second detector 374 is preferably formed of ZnCdTe, also is relatively thin and has a generally round shape in the exemplary embodiment. However, unlike elements 380 and 382, detector 374 is designed such that absorption is most probable and scattering is relatively unlikely. Detector 374 is placed within channel 378 and thereafter, detector 372 is also placed within channel 378 such that first detector unit 380 faces outwardly of channel 378. Although not illustrated, each of detector 374 and elements 380 and 382 is linked to processor 354 via a bus cable 364. Each of elements 380 and 382 and detector 374 is capable of providing signals to processor 354 which can be used to determine the locations, times and energy depositions of scattering and absorption events therein.

Orientation tracking device 356 is linked to three signal sensors 386, 388 and 390. Sensors 386, 388 and 390 are positioned about a room in which probe 352 is used and receive signals from each of transmitters 366 and 367. All of the signals generated by sensors 386, 388 and 390 are provided to tracking device 356. Tracking device 356 uses the received signals and a triangulation method similar to a global positioning system to determine the precise locations of transmitters 366 and 367. Because each of transmitters 366 and 367 is rigidly positioned with respect to camera 359 and hence with respect to first detector 380, by identifying the precise locations of transmitters 366 and 367, tracking device 356 can precisely determine the location and orientation of first detector element 380 and the other detector elements 382. The position and orientation of detector element 380 are provided to processor 354.

Processor 354 uses all of the received signals to determine the precise locations of photons which are scattered and absorbed by camera 356 and uses the source locations to generate an image, the image being displayed on display 355.

In operation, during a surgical procedure which is used to locate tumorous tissue within a patient, a surgeon inserts camera 359 into a patient's body in the vicinity of the tumor. Then, the surgeon manipulates camera 359 within the patient until photons enter the entrance window defined by first detector 380. When photons enter detector element 380, processor 354 generates an image of the photons in real time and displays the image on display 355 for the surgeon to view. As the surgeon moves camera 359 closer to the tumor, the number of photons detected becomes more intense and the image on display 355 becomes more vivid. Once the physician places element 380 adjacent the tumor, detector element 380 begins to detect positrons which only travel a small distance (e.g., 200 microns) within the patient prior to annihilation events causing photon generation. Positrons do not impact elements 382 as those elements are too far from the source to detect. When positrons are identified, the surgeon knows that tumorous tissue has been located. If desired, positrons may be displayed on display 355 in a different manner (e.g. via a different color) than photons to clearly identify proximity to tumorous tissue.

The shield 376 may have a variable configuration to permit it to be used to control directional sensitivity of camera 359. When there is no shielding, camera 359 is an omnidirectional imager.

In addition to the elements illustrated in FIG. 10, it is contemplated that a small video camera may be attached to distal handle end 362 to provide a surgeon with a view of the internal anatomy of a patient. Moreover, a fiber optic conduit for laser radiation may be provided and/or a suction unit for removing tissue debris may be mounted to end 362.

Furthermore, PMTs may be replaced by solid state photosensors and the second detector units may be replaced with solid state radiation detectors such as CZT for all systems described herein.

To apprize the public of the scope of this invention, the following claims are made:

What is claimed is:

1. An imaging system for use with a photon source disposed within an imaging area and generating photons having an energy within a known energy range, the system for determining the location of the source and comprising:

first and second oppositely facing detector pairs disposed on opposite sides of the imaging area, each pair comprising:

a first detector unit, when photons enter the first unit, the first unit scattering at least a portion of the photons during scattering events along trajectories having random angles and generating signals indicative of scattering event locations, times and energy deposits;

a second detector unit juxtaposed with respect to the first detector unit such that at least a portion of the scattered photons impinge upon the second unit and are absorbed thereby during absorption events, upon an absorption event, the second unit generating signals indicative of the energy absorbed during the absorption event and absorption event times; and a processor receiving the signals from the first and second detectors and mathematically combining those signals to determine the photon source.

2. The system of claim 1 wherein each first detector unit includes at least one solid state detector.

3. The system of claim 1 wherein each first detector unit is capable of determining scattering event locations within three detector dimensions.

4. The system of claim 3 wherein each first detector unit includes at least two planar solid state detectors which are positioned adjacent each other in parallel planes, solid state detector signals useable to determine scattering event locations within the detector plane, the third dimension of scattering event locations determined by which of the solid state detectors generates event signals.

5. The system of claim 4 wherein an imaging axis passes through the imaging area and the parallel planes are parallel to the imaging axis.

6. The system of claim 4 wherein an imaging axis passes through the imaging area and the parallel planes are perpendicular to the imaging axis.

7. The system of claim 1 wherein the source causes annihilation events which generate photon pairs including first and second photons which travel in essentially opposite directions and which are detected by the first and second oppositely facing detector pairs, the processor further includes first and second processing units corresponding to the first and second detector pairs, respectively, each processing unit including energy, timing and location (ETL) circuitry, coincidence circuitry, a summing circuit and a comparator, the ETL circuitry receiving signals form the detector units, identifying scattering and absorption event times and energies and identifying scattering event locations, the coincident circuitry identifying coincident absorption and scattering events, the summing circuit adding absorption and scattering event energies generating a sensed energy for each detected photon and the comparator comparing the sensed energies to the known energy range, the comparator identifying photons having sensed energies within the known energy range as dual detected photons.

8. The system of claim 7 wherein single detected photons include non-dual detected photons which cause scattering events, the system further including system coincidence circuitry, the comparators providing scattering event time and location signals to the system coincidence circuitry for each dual detected photon, the system coincidence circuitry comparing scattering times of each dual detected photon to identify coincident scattering events and providing coincident scattering event locations as event pairs which are indicative of photon source location.

9. The system of claim 7 wherein each second detector unit also generates signals indicative of absorption event locations and wherein the processor also mathematically combines the absorption event locations with the other received signals to determine the photon source.

10. The system of claim 9 wherein single detected photons include non-dual detected photons which cause scattering events, the system further includes system coincidence circuitry, the comparators providing scattering event time and location signals to the system coincidence circuitry for each single detected photon and each dual detected photon, the system coincidence circuitry comparing scattering event times of the photons to identify coincident scattering events and identifying coincident scattering events as event sets.

11. The system of claim 10 wherein, when two dual detected photons correspond to coincident scattering events, the system coincidence circuitry identifies the coincident event locations as an event pair.

12. The system of claim 10 wherein the system further includes a Compton processor and, when a dual detected photon is not coincident with another event, the Compton processor retrieves the scattering and absorption event data and mathematically combines the retrieved data to determine possible pre-detection paths of the dual detected photon.

13. The system of claim 10 wherein, when a dual detected photon is only coincident with one single detected photon, the system coincidence circuitry identifies the scattering event locations of the coincident single and dual detected photons as an event pair.

14. The system of claim 10 wherein the system further includes a Compton processor and, when an event set includes more than two scattering locations and one of the locations corresponds to a dual detected photon, the Compton processor retrieves the scattering and absorption data corresponding to the dual detected photon, mathematically combines the retrieved data to determine possible pre-detection paths of the dual detected photon, determines if one of the other scattering events is path bound along one of the possible paths and, where one of the scattering events is path bound, identifies the dual detected photon scattering event and the path bound event locations as an event pair.

15. The system of claim 9 wherein at least a portion of the photons directed at the first and second detector pairs fail to scatter in the first detector units and are absorbed in a second detector unit thereby generating absorption signals indicating absorption time, location and energy, for these absorbed photons, the comparator also comparing the absorbed photon energies to the known energy range and, when an absorbed photon energy is within the known energy range, identifying the absorbed photon as a single detected photon, the system further including system coincidence circuitry, the comparators providing scattering event time and location data corresponding to the dual detected photons and absorption event time and location data to the system coincidence circuitry, the system coincidence circuitry comparing scattering event and absorption event times to identify coincident events and identifying coincident event locations as event sets.

16. The system of claim 15 wherein, when a dual detected photon is only coincident with one single detected photon, the system coincidence circuitry identifies the scattering event location of the dual detected photon and the absorption event location of the single detected photon as an event pair.

17. The system of claim the system of claim 16 further including a second unit positioned outside the imaging area.

18. The system of claim 15 wherein, when an event set includes only two single detected events, the system coincidence circuitry identifies the set events as an event pair.

19. The system of claim 15 wherein the system further includes a Compton processor and, when an event set includes more than two event locations and one of the locations corresponds to a dual detected photon, the Compton processor retrieves the scattering and absorption data corresponding to the dual detected photon, mathematically combines the retrieved data to determine possible pre-detection paths of the dual detected photon, determines if one of the other scattering events is path bound along one of the possible paths and, where one of the scattering events is path bound, identifies the dual detected photon scattering event and the path bound event locations as an event pair.

20. The system of claim 1 wherein each second detector unit also generates signals indicative of absorption event locations and wherein the processor also mathematically combines the absorption event locations with the other received signals to determine the photon source.

21. The system of claim 1 including first a first annular camera which surrounds the imaging area and includes the first detector units and a second annular camera which surrounds the first annular camera and includes the second detector units.

22. The system of claim 1 wherein the second detector unit is a scintillation detector including a scintillation crystal and a plurality of photo multiplier tubes.

23. The system of claim 22 wherein each first detector unit is generally arranged along a plane and each second detector unit forms an open faced cavity wherein the open face opens toward the imaging area.

24. A method for use with a photon source disposed within an imaging area and generating photon pairs which travel in opposite directions, each photon having energy within a known energy range, the method for determining the location of the source and comprising the steps of:
for each oppositely traveling photon:
intercepting the photon at a scattering event location thereby causing the photon to deposit scattering event energy and to scatter random a new trajectory;
determining the scattering event location;
determining the scattering event energy;
absorbing the scattered photon thereby causing the photon to deposit absorption event energy;
determining the absorption event energy;
mathematically combining the scattering and absorption event energies to yield a sensed event energy; and
identifying coincidence event pairs which have sensed event energies within the known energy range; and
storing the coincidence event pairs as indications of the location of the photon source.

25. The method of claim 24 further including the steps of, for each oppositely traveling photon, determining the scatter event time and the absorption event time and, prior to mathematically combining event energies, identifying coincident scattering and absorption events and wherein the step of mathematically combining is only performed for coincident scattering and absorption events.

26. The method of claim 24 wherein the step of mathematically combining includes the step of adding the scattering and absorption event energies.

27. The method of claim 24 wherein the step of intercepting includes providing a Compton scattering detector in the path of the photon.

28. The method of claim 24 wherein the step of absorbing includes the step of providing a scintillation detector in the path of the scattered photons.

29. An imaging system for use with a photon source disposed within a portion of an object wherein a surface of the object adjacent the portion is characterized by a surface shape, the object within an imaging area, the source generating photons having energies within a known energy range, the system for determining the location of the source and comprising:
at least one first detector unit having a detector surface and positioned within the imaging area, when photons enter the first unit, the first unit scattering the photons along trajectories having random angles and generating signals indicative of scattering event locations and energy deposits, the detector surface having a topology which mirrors the surface shape such that the object portion and the detector surface are complimentary;
a second detector unit positioned outside the imaging area, when photons enter the second unit, the second unit absorbing the photons and generating signals indicative of absorbing event locations and energy deposits; and
a processor receiving the signals from the first and second detectors and mathematically combining those signals to determine the photon source.

30. The system of claim 29 wherein the first unit is moveable with respect to the second unit, the system further includes a relative position determiner which indicates the relative positions of the first and second units and the processor mathematically combines as a function of the relative positions of the first and second units.

31. The system of claim 29 wherein the portion is a breast and the first detector surface shape is generally the shape of a breast.

32. The system of claim 29 wherein a second photon source is disposed within a second portion of the object, the second source generating photons within the known energy range, the system also for blocking interference from the second source when determining location of the first source, to this end, the system further comprising a collimator juxtaposed with respect to the first unit so as to block photons from the second source from entering the first unit.

33. The system of claim 32 wherein the collimator is a shield.

34. The system of claim 29 wherein the first detector unit is C shaped.

35. The system of claim 29 wherein the first detector unit is a three dimensional detector which generates signals indicating the scattering location along three perpendicular axis.

36. The system of claim 29 wherein the first detector unit is semi-spherically shaped.

37. The system of claim 29 wherein the first detector is elongated and the detector surface is omnidirectional.

38. The system of claim 29 also for use with a second photon source disposed within a second portion of the object wherein a second surface of the object adjacent the second portion is characterized by a second surface shape, the second source also generating photons having energies within a known energy range, the system also for determining the location of the second source and further comprising:
at least a second first detector unit having a detector surface and positioned within the imaging area, when photons enter the second first unit, the second first unit scattering the photons along trajectories having random angles and generating signals indicative of scattering event locations and energy deposits, the second first unit detector surface having a topology which mirrors the second surface shape such that the object portion and the detector surface are complimentary.

39. The system of claim 29 further including an imaging processor which receives photon source location information from the processor and generated an image of the source for display.

40. An imaging system for use with a photon source disposed within an object which is in turn within an imaging area, the source generating photons having energies within a known energy range, the system for determining the location of the source and comprising:

a probe member having a distal end which is forcible into the object;

a camera mounted to the distal end, the camera comprising:

a first detector unit having a detector surface, when photons enter the first unit, the first unit scattering the photons along trajectories having random angles and generating signals indicative of scattering event locations and energy deposits;

a second detector unit positioned with respect to the first unit such that at least a portion of the scattered photons impinge on the second unit, when photons impinge on the second unit, the second unit absorbing the photons and generating signals indicative of absorbing event locations and energy deposits; and a processor receiving the signals from the first and second detectors and mathematically combining those signals to determine the photon source.

41. The system of claim 40 further including an orientation tracking device which determines the position and orientation of the camera and provides position and orientation data to the processor, the processor also mathematically combining the position and orientation information to determine the photon source.

42. The system of claim 40 further including an imaging processor which receives photon source location information from the processor and generated an image of the source for display.

43. The system of claim 40 wherein the first detector unit is a three dimensional detector which generates signals indicating the scattering location along three perpendicular axis.

44. The system of claim 40 also for use with the source wherein the source emits positrons, when a positron enters the first detector unit, the first detector unit sensing the positron and generating signals indicating the location of the positron detection.

45. The system of claim 40 further including a photon shield mounted to the distal end adjacent the first unit so as to block photons from entering the first unit along at least one path.

* * * * *